(12) United States Patent
Bracy et al.

(10) Patent No.: US 12,274,436 B2
(45) Date of Patent: Apr. 15, 2025

(54) SUTURE TOOL AND METHOD OF USE

(71) Applicant: PARCUS MEDICAL, LLC, Sarasota, FL (US)

(72) Inventors: Barton Bracy, Orlando, FL (US); Mark D Brunsvold, Sarasota, FL (US); Joel M. Harshbarger, Palmetto, FL (US)

(73) Assignee: PARCUS MEDICAL, LLC, Sarasota, FL (US)

( * ) Notice: Subject to any disclaimer, the term of this patent is extended or adjusted under 35 U.S.C. 154(b) by 205 days.

(21) Appl. No.: 17/958,391

(22) Filed: Oct. 1, 2022

(65) Prior Publication Data

US 2023/0021371 A1    Jan. 26, 2023

Related U.S. Application Data

(63) Continuation of application No. 16/206,736, filed on Nov. 30, 2018, now Pat. No. 11,457,912, which is a continuation of application No. PCT/US2017/035792, filed on Jun. 2, 2017.

(60) Provisional application No. 62/368,023, filed on Jul. 28, 2016, provisional application No. 62/344,489, filed on Jun. 2, 2016.

(51) Int. Cl.
*A61B 17/04* (2006.01)
*A61B 17/00* (2006.01)

(52) U.S. Cl.
CPC ...... *A61B 17/0469* (2013.01); *A61B 17/0401* (2013.01); *A61B 17/0482* (2013.01); *A61B 17/0485* (2013.01); *A61B 2017/00349* (2013.01); *A61B 2017/0409* (2013.01); *A61B 2017/044* (2013.01); *A61B 2017/0445* (2013.01); *A61B 2017/0446* (2013.01)

(58) Field of Classification Search
CPC ..... A61B 17/00; A61B 17/04; A61B 17/0401; A61B 17/0469; A61B 17/0482; A61B 17/0485; A61B 17/3468; A61B 2017/0446; A61B 2017/0409; A61B 2017/0482; A61B 2017/0414
See application file for complete search history.

(56) References Cited

U.S. PATENT DOCUMENTS

| | | |
|---|---|---|
| 5,203,787 A | 4/1993 | Noblitt et al. |
| 5,207,679 A | 5/1993 | Li |
| 5,527,316 A | 6/1996 | Stone et al. |
| 5,578,036 A | 11/1996 | Stone et al. |
| 5,591,207 A * | 1/1997 | Coleman ............ A61B 17/0401 606/301 |

(Continued)

OTHER PUBLICATIONS

File History for U.S. Appl. No. 16/206,736 as accessed from U.S. Patent and Trademark Office.

(Continued)

*Primary Examiner* — Vi X Nguyen
(74) *Attorney, Agent, or Firm* — GOODWIN PROCTER LLP

(57) ABSTRACT

A surgical tool incorporates a suture guide and anchor driver supporting an anchor where the anchor is maintained at a distance from the suture guide until release of a detent mechanism. Thereafter, the anchor is allowed to move into proximity to the suture guide, fixing a suture supported by the suture guide to a substrate, the entire procedure being achievable with a single hand.

10 Claims, 22 Drawing Sheets

(56) References Cited

U.S. PATENT DOCUMENTS

| | | |
|---|---|---|
| 5,660,091 A | 8/1997 | Stone et al. |
| 5,690,631 A | 11/1997 | Duncan et al. |
| 5,702,396 A | 12/1997 | Hoenig et al. |
| 5,732,821 A | 3/1998 | Stone et al. |
| 5,792,143 A | 8/1998 | Samuelsson et al. |
| 5,948,000 A | 9/1999 | Larsen et al. |
| 6,024,759 A | 2/2000 | Nuss et al. |
| 6,129,728 A | 10/2000 | Schumacher et al. |
| 6,325,803 B1 | 12/2001 | Schumacher et al. |
| 6,364,910 B1 | 4/2002 | Shultz et al. |
| 6,471,706 B1 | 10/2002 | Schumacher et al. |
| 6,616,673 B1 | 9/2003 | Stone et al. |
| 6,641,597 B2 | 11/2003 | Burkhart et al. |
| 6,685,707 B2 | 2/2004 | Roman et al. |
| 6,746,486 B1 | 6/2004 | Shultz et al. |
| 6,783,549 B1 | 8/2004 | Stone et al. |
| 6,942,699 B2 | 9/2005 | Stone et al. |
| 7,175,663 B1 | 2/2007 | Stone |
| 7,217,246 B1 | 5/2007 | Stone |
| 7,247,170 B2 | 7/2007 | Graham et al. |
| 7,252,832 B1 | 8/2007 | Stone et al. |
| 7,323,012 B1 | 1/2008 | Stone et al. |
| 7,329,272 B2 | 2/2008 | Burkhart et al. |
| 7,331,982 B1 | 2/2008 | Kaiser et al. |
| 7,338,528 B2 | 3/2008 | Stone et al. |
| 7,341,592 B1 | 3/2008 | Walters et al. |
| 7,488,323 B2 | 2/2009 | Bacastow et al. |
| 7,500,983 B1 | 3/2009 | Kaiser et al. |
| 7,572,265 B2 | 8/2009 | Stone et al. |
| 7,601,165 B2 | 10/2009 | Stone |
| 7,604,636 B1 | 10/2009 | Walters et al. |
| 7,604,666 B2 | 10/2009 | Berelsman et al. |
| 7,608,098 B1 | 10/2009 | Stone et al. |
| 7,621,961 B2 | 11/2009 | Stone |
| 7,625,406 B2 | 12/2009 | Berelsman et al. |
| 7,658,751 B2 | 2/2010 | Stone et al. |
| 7,674,276 B2 | 3/2010 | Stone et al. |
| 7,695,503 B1 | 4/2010 | Kaiser et al. |
| 7,713,285 B1 | 5/2010 | Stone et al. |
| 7,722,630 B1 | 5/2010 | Stone et al. |
| 7,736,364 B2 | 6/2010 | Stone |
| 7,749,226 B2 | 7/2010 | Stone |
| 7,749,250 B2 | 7/2010 | Stone et al. |
| 7,758,643 B2 | 7/2010 | Stone et al. |
| 7,766,964 B2 | 8/2010 | Stone et al. |
| 7,776,077 B2 | 8/2010 | Kaiser et al. |
| 7,794,484 B2 | 9/2010 | Stone et al. |
| 7,803,173 B2 | 9/2010 | Burkhart et al. |
| 7,819,881 B2 | 10/2010 | Stone et al. |
| 7,819,898 B2 | 10/2010 | Stone et al. |
| 7,819,923 B2 | 10/2010 | Stone et al. |
| 7,828,751 B2 | 11/2010 | Stone |
| 7,828,820 B2 | 11/2010 | Stone et al. |
| 7,850,711 B1 | 12/2010 | Stone et al. |
| 7,857,830 B2 | 12/2010 | Stone et al. |
| 7,879,055 B1 | 2/2011 | Stone et al. |
| 7,896,917 B2 | 3/2011 | Walters et al. |
| 7,905,903 B2 | 3/2011 | Stone et al. |
| 7,905,904 B2 | 3/2011 | Stone et al. |
| 7,909,851 B2 | 3/2011 | Stone et al. |
| 7,914,539 B2 | 3/2011 | Stone et al. |
| 7,959,650 B2 | 6/2011 | Kaiser et al. |
| 7,959,680 B2 | 6/2011 | Stone et al. |
| 7,967,843 B2 | 6/2011 | Kaiser et al. |
| 7,981,140 B2 | 7/2011 | Burkhart et al. |
| 7,998,204 B2 | 8/2011 | Stone et al. |
| 8,012,174 B2 | 9/2011 | Elattrache et al. |
| 8,034,090 B2 | 10/2011 | Stone et al. |
| 8,057,489 B2 | 11/2011 | Stone et al. |
| 8,062,376 B2 | 11/2011 | Shultz et al. |
| 8,088,130 B2 | 1/2012 | Kaiser et al. |
| 8,105,390 B2 | 1/2012 | Shultz et al. |
| 8,109,965 B2 | 2/2012 | Stone et al. |
| 8,118,836 B2 | 2/2012 | Denham et al. |
| 8,123,813 B2 | 2/2012 | Metzger et al. |
| 8,128,658 B2 | 3/2012 | Kaiser et al. |
| 8,137,354 B2 | 3/2012 | Stone |
| 8,137,382 B2 | 3/2012 | Denham et al. |
| 8,142,502 B2 | 3/2012 | Stone et al. |
| 8,147,546 B2 | 4/2012 | Stone et al. |
| 8,162,967 B1 | 4/2012 | Kaiser et al. |
| 8,197,482 B2 | 6/2012 | Stone |
| 8,202,296 B2 | 6/2012 | Burkhart |
| 8,202,297 B2 | 6/2012 | Burkhart |
| 8,231,654 B2 | 7/2012 | Kaiser et al. |
| 8,236,059 B2 | 8/2012 | Stone et al. |
| 8,241,293 B2 | 8/2012 | Stone et al. |
| 8,241,305 B2 | 8/2012 | Stone |
| 8,251,998 B2 | 8/2012 | Hoeppner et al. |
| 8,273,106 B2 | 9/2012 | Stone et al. |
| 8,287,544 B2 | 10/2012 | Stone |
| 8,292,921 B2 | 10/2012 | Stone et al. |
| 8,298,262 B2 | 10/2012 | Stone et al. |
| 8,303,604 B2 | 11/2012 | Stone et al. |
| 8,308,780 B2 | 11/2012 | Kaiser et al. |
| 8,317,825 B2 | 11/2012 | Stone |
| 8,317,871 B2 | 11/2012 | Stone et al. |
| 8,337,525 B2 | 12/2012 | Stone et al. |
| 8,343,227 B2 | 1/2013 | Metzger et al. |
| 8,361,113 B2 | 1/2013 | Stone et al. |
| 8,361,114 B2 | 1/2013 | Stone et al. |
| 8,372,154 B2 | 2/2013 | Schultz et al. |
| 8,409,253 B2 | 4/2013 | Stone et al. |
| 8,419,794 B2 | 4/2013 | Elattrache et al. |
| 8,444,659 B2 | 5/2013 | Stone et al. |
| 8,465,522 B2 | 6/2013 | Burkhart |
| 8,491,609 B2 | 7/2013 | Stone |
| 8,491,632 B2 | 7/2013 | Stone et al. |
| 8,500,818 B2 | 8/2013 | Metzger et al. |
| 8,506,596 B2 | 8/2013 | Stone et al. |
| 8,506,597 B2 | 8/2013 | Kaiser et al. |
| 8,535,357 B2 | 9/2013 | Stone et al. |
| 8,551,140 B2 | 10/2013 | Denham et al. |
| 8,551,180 B2 | 10/2013 | Shultz et al. |
| 8,562,645 B2 | 10/2013 | Stone et al. |
| 8,562,647 B2 | 10/2013 | Kaiser et al. |
| 8,574,235 B2 | 11/2013 | Stone |
| 8,574,275 B2 | 11/2013 | Stone et al. |
| 8,585,768 B2 | 11/2013 | Berelsman et al. |
| 8,597,327 B2 | 12/2013 | Stone et al. |
| 8,603,125 B2 | 12/2013 | Stone et al. |
| 8,608,777 B2 | 12/2013 | Kaiser et al. |
| 8,632,547 B2 | 1/2014 | Maxson et al. |
| 8,632,569 B2 | 1/2014 | Stone et al. |
| 8,652,171 B2 | 2/2014 | Stone et al. |
| 8,652,172 B2 | 2/2014 | Denham et al. |
| 8,663,279 B2 | 3/2014 | Burkhart et al. |
| 8,672,968 B2 | 3/2014 | Stone et al. |
| 8,672,969 B2 | 3/2014 | Stone et al. |
| 8,679,135 B2 | 3/2014 | Stone et al. |
| 8,696,688 B2 | 4/2014 | Stone |
| 8,702,804 B2 | 4/2014 | Smith et al. |
| 8,709,022 B2 | 4/2014 | Stone et al. |
| 8,721,684 B2 | 5/2014 | Denham et al. |
| 8,771,316 B2 | 7/2014 | Denham et al. |
| 8,771,351 B2 | 7/2014 | Elattrache et al. |
| 8,771,352 B2 | 7/2014 | Conner et al. |
| 8,777,956 B2 | 7/2014 | Hoeppner et al. |
| 8,784,489 B2 | 7/2014 | Walters et al. |
| 8,795,379 B2 | 8/2014 | Smith et al. |
| 8,801,783 B2 | 8/2014 | Stone et al. |
| 8,828,087 B2 | 9/2014 | Stone et al. |
| 8,834,573 B2 | 9/2014 | Metzger et al. |
| 8,840,645 B2 | 9/2014 | Denham et al. |
| 8,845,685 B2 | 9/2014 | Stone et al. |
| 8,864,769 B2 | 10/2014 | Stone et al. |
| 8,900,301 B2 | 12/2014 | Stone et al. |
| 8,900,314 B2 | 12/2014 | Metzger et al. |
| 8,906,103 B2 | 12/2014 | Stone et al. |
| 8,926,613 B2 | 1/2015 | Kaiser et al. |
| 8,932,331 B2 | 1/2015 | Kaiser et al. |
| 8,936,621 B2 | 1/2015 | Denham et al. |
| 8,939,983 B2 | 1/2015 | Stone et al. |
| 8,968,364 B2 | 3/2015 | Berelsman et al. |

(56) References Cited

U.S. PATENT DOCUMENTS

| | | |
|---|---|---|
| 8,986,345 B2 | 3/2015 | Denham et al. |
| 8,998,949 B2 | 4/2015 | Stone et al. |
| 9,005,246 B2 | 4/2015 | Burkhart et al. |
| 9,005,287 B2 | 4/2015 | Stone |
| 9,017,381 B2 | 4/2015 | Kaiser et al. |
| 9,078,644 B2 | 7/2015 | Stone |
| 9,101,373 B2 | 8/2015 | Norton et al. |
| 9,149,267 B2 | 10/2015 | Norton et al. |
| 9,173,651 B2 | 11/2015 | Stone et al. |
| 9,179,907 B2 | 11/2015 | Elattrache et al. |
| 9,198,673 B2 | 12/2015 | Stone |
| 9,211,184 B2 | 12/2015 | Stone et al. |
| 9,216,078 B2 | 12/2015 | Conner et al. |
| 9,226,817 B2 | 1/2016 | Dougherty et al. |
| 9,232,939 B2 | 1/2016 | Denham et al. |
| 9,237,887 B2 | 1/2016 | Wack et al. |
| 9,241,803 B2 | 1/2016 | Stone et al. |
| 9,259,217 B2 | 2/2016 | Fritzinger et al. |
| 9,271,713 B2 | 3/2016 | Denham et al. |
| 9,271,720 B2 | 3/2016 | Stone et al. |
| 9,314,241 B2 | 4/2016 | Stone et al. |
| 9,326,763 B2 | 5/2016 | Stone et al. |
| 9,326,862 B2 | 5/2016 | Smith et al. |
| 9,357,992 B2 | 6/2016 | Stone et al. |
| 9,381,021 B2 | 7/2016 | Wagner et al. |
| 9,398,906 B2 | 7/2016 | Stone et al. |
| 9,402,621 B2 | 8/2016 | Stone et al. |
| 9,408,599 B2 | 8/2016 | Kaiser et al. |
| 9,414,833 B2 | 8/2016 | Stone et al. |
| 9,414,925 B2 | 8/2016 | Metzger et al. |
| 9,433,406 B2 | 9/2016 | Slagle et al. |
| 9,433,407 B2 | 9/2016 | Fritzinger et al. |
| 9,439,645 B2 | 9/2016 | Stone et al. |
| 9,445,827 B2 | 9/2016 | Kaiser et al. |
| 9,456,833 B2 | 10/2016 | Maxson et al. |
| 9,468,433 B2 | 10/2016 | Denham et al. |
| 9,486,211 B2 | 11/2016 | Stone et al. |
| 9,492,158 B2 | 11/2016 | Stone et al. |
| 9,498,204 B2 | 11/2016 | Denham et al. |
| 9,504,460 B2 | 11/2016 | Stone et al. |
| 9,510,819 B2 | 12/2016 | Stone et al. |
| 9,510,821 B2 | 12/2016 | Denham et al. |
| 9,532,775 B2 | 1/2017 | Stone et al. |
| 9,532,777 B2 | 1/2017 | Kaiser et al. |
| 9,538,998 B2 | 1/2017 | Stone et al. |
| 9,539,003 B2 | 1/2017 | Stone et al. |
| 9,561,025 B2 | 2/2017 | Stone et al. |
| 9,572,563 B2 | 2/2017 | Berelsman et al. |
| 9,572,655 B2 | 2/2017 | Denham et al. |
| 9,592,061 B2 | 3/2017 | Norton et al. |
| 9,603,591 B2 | 3/2017 | Denham et al. |
| 9,622,736 B2 | 4/2017 | Stone et al. |
| 9,622,851 B2 | 4/2017 | Stone et al. |
| 9,642,661 B2 | 5/2017 | Stone et al. |
| 9,662,107 B2 | 5/2017 | Stone et al. |
| 9,681,940 B2 | 6/2017 | Stone et al. |
| 9,687,225 B2 | 6/2017 | Palese et al. |
| 9,700,423 B2 | 7/2017 | Stone et al. |
| 9,724,090 B2 | 8/2017 | Kaiser et al. |
| 9,757,119 B2 | 9/2017 | Norton et al. |
| 9,763,656 B2 | 9/2017 | Stone et al. |
| 9,763,800 B2 | 9/2017 | Finley et al. |
| 9,788,876 B2 | 10/2017 | Stone et al. |
| 9,801,620 B2 | 10/2017 | Kaiser et al. |
| 9,801,708 B2 | 10/2017 | Denham et al. |
| 9,827,011 B2 | 11/2017 | Cresina et al. |
| 9,833,230 B2 | 12/2017 | Stone |
| 9,861,351 B2 | 1/2018 | Kaiser et al. |
| 9,907,548 B2 | 3/2018 | Dougherty et al. |
| 9,918,826 B2 | 3/2018 | Berelsman et al. |
| 9,918,827 B2 | 3/2018 | Berelsman et al. |
| 9,955,980 B2 | 5/2018 | Norton et al. |
| 9,974,534 B2 | 5/2018 | Troxel et al. |
| 9,993,241 B2 | 6/2018 | Denham et al. |
| 10,004,489 B2 | 6/2018 | Kaiser et al. |
| 10,004,493 B2 | 6/2018 | Stone et al. |
| 10,004,588 B2 | 6/2018 | Berelsman et al. |
| 10,022,118 B2 | 7/2018 | Norton et al. |
| 10,034,758 B2 | 7/2018 | Winslow et al. |
| 10,052,092 B2 | 8/2018 | Finley et al. |
| 10,092,288 B2 | 9/2018 | Denham et al. |
| 10,098,629 B2 | 10/2018 | Kaiser et al. |
| 10,130,355 B2 | 11/2018 | Denham et al. |
| 10,136,886 B2 | 11/2018 | Norton et al. |
| 10,149,767 B2 | 12/2018 | Metzger et al. |
| 10,154,837 B2 | 12/2018 | Stone et al. |
| 10,166,022 B2 | 1/2019 | Early et al. |
| 10,166,032 B2 | 1/2019 | Stone et al. |
| 10,285,689 B2 | 5/2019 | Finley et al. |
| 10,321,906 B2 | 6/2019 | Stone et al. |
| 10,349,931 B2 | 7/2019 | Stone |
| 10,368,856 B2 | 8/2019 | Stone et al. |
| 10,398,428 B2 | 9/2019 | Denham et al. |
| 10,398,430 B2 | 9/2019 | Stone et al. |
| 10,441,264 B2 | 10/2019 | Stone et al. |
| 10,485,532 B2 | 11/2019 | Norton et al. |
| 10,517,587 B2 | 12/2019 | Denham et al. |
| 10,517,714 B2 | 12/2019 | Stone et al. |
| 10,537,373 B2 | 1/2020 | Hoeppener et al. |
| 10,542,967 B2 | 1/2020 | Kaiser et al. |
| 10,595,851 B2 | 3/2020 | Kaiser et al. |
| 10,603,029 B2 | 3/2020 | Kaiser et al. |
| 10,603,181 B2 | 3/2020 | Stone et al. |
| 10,610,217 B2 | 4/2020 | Stone et al. |
| 10,631,843 B2 | 4/2020 | Stone et al. |
| 10,639,023 B2 | 5/2020 | Berelsman et al. |
| 10,675,073 B2 | 6/2020 | Stone et al. |
| 10,687,803 B2 | 6/2020 | Denham et al. |
| 10,695,045 B2 | 6/2020 | Kaiser et al. |
| 10,695,052 B2 | 6/2020 | Denham et al. |
| 10,702,259 B2 | 7/2020 | Stone et al. |
| 10,716,557 B2 | 7/2020 | Denham et al. |
| 10,729,421 B2 | 8/2020 | Stone et al. |
| 10,729,423 B2 | 8/2020 | Kaiser et al. |
| 10,729,430 B2 | 8/2020 | Denham et al. |
| 10,729,552 B2 | 8/2020 | Finley et al. |
| 10,743,925 B2 | 8/2020 | Stone et al. |
| 10,758,221 B2 | 9/2020 | Berelsman et al. |
| 10,806,443 B2 | 10/2020 | Norton et al. |
| 10,835,232 B2 | 11/2020 | Stone |
| 10,842,478 B2 | 11/2020 | Hoeppner et al. |
| 10,842,481 B2 | 11/2020 | Palese et al. |
| 10,912,551 B2 | 2/2021 | Troxel et al. |
| 10,932,770 B2 | 3/2021 | Stone et al. |
| 10,966,704 B2 | 4/2021 | Lozier et al. |
| 10,973,507 B2 | 4/2021 | Stone et al. |
| 10,987,099 B2 | 4/2021 | Stone et al. |
| 11,039,826 B2 | 6/2021 | Denham et al. |
| 11,065,103 B2 | 7/2021 | Berelsman et al. |
| 11,096,684 B2 | 8/2021 | Stone |
| 2002/0062127 A1 | 5/2002 | Schumacher et al. |
| 2002/0115999 A1 | 8/2002 | McDevitt et al. |
| 2002/0128654 A1 | 9/2002 | Steger et al. |
| 2003/0028253 A1 | 2/2003 | Stone et al. |
| 2003/0125743 A1 | 7/2003 | Roman et al. |
| 2003/0208276 A1 | 11/2003 | Berelsman et al. |
| 2003/0229350 A1* | 12/2003 | Kay .............. A61B 17/86 470/10 |
| 2004/0127908 A1 | 7/2004 | Roman et al. |
| 2004/0153161 A1 | 8/2004 | Stone et al. |
| 2004/0254646 A1 | 12/2004 | Stone et al. |
| 2004/0260298 A1 | 12/2004 | Kaiser et al. |
| 2005/0004675 A1 | 1/2005 | Shultz et al. |
| 2005/0107882 A1 | 5/2005 | Stone et al. |
| 2005/0119696 A1 | 6/2005 | Walters et al. |
| 2005/0197708 A1 | 9/2005 | Stone et al. |
| 2005/0273003 A1 | 12/2005 | Walters et al. |
| 2005/0277961 A1 | 12/2005 | Stone et al. |
| 2006/0020344 A1 | 1/2006 | Shultz et al. |
| 2006/0029633 A1 | 2/2006 | Kaiser et al. |
| 2006/0036330 A1 | 2/2006 | Shultz et al. |
| 2006/0100627 A1 | 5/2006 | Stone et al. |
| 2006/0111729 A1 | 5/2006 | Bacastow et al. |
| 2006/0173546 A1 | 8/2006 | Berelsman et al. |

(56) References Cited

U.S. PATENT DOCUMENTS

| | | |
|---|---|---|
| 2006/0189993 A1 | 8/2006 | Stone |
| 2006/0190042 A1 | 8/2006 | Stone et al. |
| 2006/0235413 A1 | 10/2006 | Denham et al. |
| 2006/0247642 A1 | 11/2006 | Stone et al. |
| 2006/0282085 A1 | 12/2006 | Stone et al. |
| 2006/0293685 A1 | 12/2006 | Stone et al. |
| 2007/0038230 A1 | 2/2007 | Stone et al. |
| 2007/0038299 A1 | 2/2007 | Stone et al. |
| 2007/0049944 A1 | 3/2007 | Stone et al. |
| 2007/0141110 A1 | 6/2007 | Stone et al. |
| 2007/0142918 A1 | 6/2007 | Stone |
| 2007/0156174 A1 | 7/2007 | Kaiser et al. |
| 2007/0179510 A1 | 8/2007 | Stone |
| 2007/0179624 A1 | 8/2007 | Stone et al. |
| 2007/0185532 A1 | 8/2007 | Stone et al. |
| 2007/0191853 A1 | 8/2007 | Stone |
| 2007/0208294 A1 | 9/2007 | Stone |
| 2007/0225719 A1 | 9/2007 | Stone et al. |
| 2007/0225735 A1 | 9/2007 | Stone et al. |
| 2008/0015706 A1 | 1/2008 | Berelsman et al. |
| 2008/0021554 A1 | 1/2008 | Stone et al. |
| 2008/0027446 A1 | 1/2008 | Stone et al. |
| 2008/0033566 A1 | 2/2008 | Berelsman et al. |
| 2008/0065114 A1 | 4/2008 | Stone et al. |
| 2008/0082127 A1 | 4/2008 | Stone et al. |
| 2008/0082128 A1 | 4/2008 | Stone |
| 2008/0086138 A1 | 4/2008 | Stone et al. |
| 2008/0097453 A1 | 4/2008 | Stone |
| 2008/0132932 A1 | 6/2008 | Hoeppner et al. |
| 2008/0140092 A1 | 6/2008 | Stone et al. |
| 2008/0140093 A1 | 6/2008 | Stone et al. |
| 2008/0161852 A1 | 7/2008 | Kaiser et al. |
| 2008/0215055 A1 | 9/2008 | Stone |
| 2008/0228271 A1 | 9/2008 | Stone et al. |
| 2008/0243248 A1 | 10/2008 | Stone et al. |
| 2008/0249632 A1 | 10/2008 | Stone et al. |
| 2008/0255613 A1 | 10/2008 | Kaiser et al. |
| 2008/0269674 A1 | 10/2008 | Stone |
| 2008/0275431 A1 | 11/2008 | Stone et al. |
| 2008/0281325 A1 | 11/2008 | Stone et al. |
| 2008/0306490 A1 | 12/2008 | Lakin et al. |
| 2008/0312689 A1 | 12/2008 | Denham et al. |
| 2009/0054928 A1 | 2/2009 | Denham et al. |
| 2009/0062854 A1 | 3/2009 | Kaiser et al. |
| 2009/0082805 A1 | 3/2009 | Kaiser et al. |
| 2009/0192468 A1 | 7/2009 | Stone |
| 2009/0204146 A1 | 8/2009 | Kaiser et al. |
| 2009/0281555 A1 | 11/2009 | Stone |
| 2009/0306684 A1 | 12/2009 | Stone et al. |
| 2009/0306711 A1 | 12/2009 | Stone et al. |
| 2009/0312776 A1 | 12/2009 | Kaiser et al. |
| 2009/0318961 A1 | 12/2009 | Stone et al. |
| 2010/0010636 A1 | 1/2010 | Shultz et al. |
| 2010/0087857 A1 | 4/2010 | Stone et al. |
| 2010/0145384 A1 | 6/2010 | Stone et al. |
| 2010/0152782 A1 | 6/2010 | Stone et al. |
| 2010/0179661 A1 | 7/2010 | Berelsman et al. |
| 2010/0211075 A1 | 8/2010 | Stone |
| 2010/0222791 A1 | 9/2010 | Stone et al. |
| 2010/0222812 A1 | 9/2010 | Stone et al. |
| 2010/0256642 A1 | 10/2010 | Stone |
| 2010/0268233 A1 | 10/2010 | Stone |
| 2010/0268275 A1 | 10/2010 | Stone et al. |
| 2010/0286795 A1 | 11/2010 | Stone et al. |
| 2010/0292731 A1* | 11/2010 | Gittings ............ A61B 17/0401 606/232 |
| 2010/0292792 A1 | 11/2010 | Stone et al. |
| 2010/0305698 A1 | 12/2010 | Metzger et al. |
| 2010/0305709 A1 | 12/2010 | Metzger et al. |
| 2010/0312341 A1 | 12/2010 | Kaiser et al. |
| 2011/0004258 A1 | 1/2011 | Stone et al. |
| 2011/0015740 A1 | 1/2011 | Metzger et al. |
| 2011/0035015 A1 | 2/2011 | Stone et al. |
| 2011/0054526 A1 | 3/2011 | Stone et al. |
| 2011/0087284 A1 | 4/2011 | Stone et al. |
| 2011/0098727 A1 | 4/2011 | Kaiser et al. |
| 2011/0100173 A1 | 5/2011 | Stone et al. |
| 2011/0106153 A1 | 5/2011 | Stone et al. |
| 2011/0153018 A1 | 6/2011 | Walters et al. |
| 2011/0160767 A1 | 6/2011 | Stone et al. |
| 2011/0160768 A1 | 6/2011 | Stone et al. |
| 2011/0166578 A1 | 7/2011 | Stone et al. |
| 2011/0208239 A1 | 8/2011 | Stone et al. |
| 2011/0208240 A1 | 8/2011 | Stone et al. |
| 2011/0213376 A1 | 9/2011 | Maxson et al. |
| 2011/0218625 A1 | 9/2011 | Berelsman et al. |
| 2011/0224799 A1 | 9/2011 | Stone |
| 2011/0264141 A1 | 10/2011 | Denham et al. |
| 2011/0270306 A1 | 11/2011 | Denham et al. |
| 2011/0295279 A1 | 12/2011 | Stone et al. |
| 2011/0301708 A1 | 12/2011 | Stone et al. |
| 2012/0041485 A1 | 2/2012 | Kaiser et al. |
| 2012/0041486 A1 | 2/2012 | Stone et al. |
| 2012/0046693 A1 | 2/2012 | Denham et al. |
| 2012/0053630 A1 | 3/2012 | Denham et al. |
| 2012/0059417 A1 | 3/2012 | Norton et al. |
| 2012/0059418 A1 | 3/2012 | Denham et al. |
| 2012/0078375 A1 | 3/2012 | Smith et al. |
| 2012/0089193 A1 | 4/2012 | Stone et al. |
| 2012/0095470 A1 | 4/2012 | Kaiser et al. |
| 2012/0095565 A1 | 4/2012 | Shultz et al. |
| 2012/0109321 A1 | 5/2012 | Stone et al. |
| 2012/0116409 A1 | 5/2012 | Stone |
| 2012/0116452 A1 | 5/2012 | Stone et al. |
| 2012/0150297 A1 | 6/2012 | Denham et al. |
| 2012/0150307 A1 | 6/2012 | Metzger et al. |
| 2012/0165866 A1 | 6/2012 | Kaiser et al. |
| 2012/0165867 A1 | 6/2012 | Denham et al. |
| 2012/0165938 A1 | 6/2012 | Denham et al. |
| 2012/0172986 A1 | 7/2012 | Stone et al. |
| 2012/0245585 A1 | 9/2012 | Kaiser et al. |
| 2012/0245698 A1 | 9/2012 | Stone et al. |
| 2012/0296345 A1 | 11/2012 | Wack et al. |
| 2012/0296427 A1 | 11/2012 | Conner et al. |
| 2012/0303046 A1 | 11/2012 | Stone et al. |
| 2012/0310245 A1 | 12/2012 | Hoeppner et al. |
| 2013/0012962 A1 | 1/2013 | Stone |
| 2013/0023930 A1 | 1/2013 | Stone et al. |
| 2013/0035698 A1 | 2/2013 | Stone et al. |
| 2013/0046341 A1 | 2/2013 | Stone et al. |
| 2013/0079780 A1 | 3/2013 | Wagner et al. |
| 2013/0096678 A1 | 4/2013 | Denham |
| 2013/0103082 A1 | 4/2013 | Kaiser et al. |
| 2013/0110251 A1 | 5/2013 | Metzger et al. |
| 2013/0116730 A1 | 5/2013 | Denham et al. |
| 2013/0123813 A1 | 5/2013 | Stone et al. |
| 2013/0138123 A1 | 5/2013 | Stone et al. |
| 2013/0138152 A1 | 5/2013 | Stone et al. |
| 2013/0144337 A1 | 6/2013 | Stone et al. |
| 2013/0144338 A1 | 6/2013 | Stone et al. |
| 2013/0144397 A1 | 6/2013 | Smith et al. |
| 2013/0158601 A1 | 6/2013 | Stone et al. |
| 2013/0172944 A1 | 7/2013 | Fritzinger et al. |
| 2013/0184764 A1 | 7/2013 | Stone et al. |
| 2013/0190818 A1 | 7/2013 | Norton |
| 2013/0190819 A1 | 7/2013 | Norton |
| 2013/0204276 A1 | 8/2013 | Stone et al. |
| 2013/0211452 A1 | 8/2013 | Stone et al. |
| 2013/0245761 A1 | 9/2013 | Conner et al. |
| 2013/0304120 A1 | 11/2013 | Stone et al. |
| 2013/0317612 A1 | 11/2013 | Stone et al. |
| 2013/0317621 A1 | 11/2013 | Metzger et al. |
| 2013/0325063 A1 | 12/2013 | Norton et al. |
| 2013/0331848 A1 | 12/2013 | Kaiser et al. |
| 2013/0331885 A1 | 12/2013 | Stone et al. |
| 2014/0046367 A1 | 2/2014 | Stone et al. |
| 2014/0046368 A1 | 2/2014 | Kaiser et al. |
| 2014/0066982 A1 | 3/2014 | Stone et al. |
| 2014/0067081 A1 | 3/2014 | Stone |
| 2014/0074160 A1 | 3/2014 | Denham et al. |
| 2014/0088655 A1 | 3/2014 | Stone et al. |
| 2014/0094913 A1 | 4/2014 | Berelsman et al. |
| 2014/0107657 A1 | 4/2014 | Norton et al. |
| 2014/0107715 A1 | 4/2014 | Heilman et al. |

(56) References Cited

U.S. PATENT DOCUMENTS

| | | |
|---|---|---|
| 2014/0135775 A1 | 5/2014 | Maxson et al. |
| 2014/0135835 A1 | 5/2014 | Stone et al. |
| 2014/0163613 A1 | 6/2014 | Stone et al. |
| 2014/0163614 A1 | 6/2014 | Denham et al. |
| 2014/0194927 A1 | 7/2014 | Kaiser et al. |
| 2014/0200583 A1 | 7/2014 | Stone et al. |
| 2014/0207158 A1 | 7/2014 | Stone et al. |
| 2014/0214100 A1 | 7/2014 | Norton |
| 2014/0236191 A1 | 8/2014 | Stone et al. |
| 2014/0236309 A1 | 8/2014 | Smith et al. |
| 2014/0257378 A1 | 9/2014 | Norton et al. |
| 2014/0276819 A1 | 9/2014 | Cresina et al. |
| 2014/0276826 A1 | 9/2014 | Metzinger et al. |
| 2014/0276992 A1 | 9/2014 | Stone et al. |
| 2014/0277447 A1 | 9/2014 | Berelsman et al. |
| 2014/0296988 A1 | 10/2014 | Winslow et al. |
| 2014/0324101 A1 | 10/2014 | Denham et al. |
| 2014/0330311 A1 | 11/2014 | Denham et al. |
| 2014/0350674 A1 | 11/2014 | Stone et al. |
| 2014/0364906 A1 | 12/2014 | Palese et al. |
| 2014/0378979 A1 | 12/2014 | Stone et al. |
| 2015/0005820 A1 | 1/2015 | Finley et al. |
| 2015/0012015 A1 | 1/2015 | Berelsman et al. |
| 2015/0012016 A1 | 1/2015 | Stone |
| 2015/0012094 A1 | 1/2015 | Denham et al. |
| 2015/0018880 A1 | 1/2015 | Stone et al. |
| 2015/0025643 A1 | 1/2015 | Stone et al. |
| 2015/0057757 A1 | 2/2015 | Metzger et al. |
| 2015/0073417 A1 | 3/2015 | Norton et al. |
| 2015/0094739 A1 | 4/2015 | Norton et al. |
| 2015/0119890 A1 | 4/2015 | Kaiser et al. |
| 2015/0127051 A1 | 5/2015 | Kaiser et al. |
| 2015/0134000 A1 | 5/2015 | Denham et al. |
| 2015/0134001 A1 | 5/2015 | Stone et al. |
| 2015/0141995 A1 | 5/2015 | Norton |
| 2015/0173742 A1 | 6/2015 | Palese et al. |
| 2015/0173743 A1 | 6/2015 | Palese et al. |
| 2015/0173754 A1 | 6/2015 | Norton et al. |
| 2015/0173887 A1 | 6/2015 | Berelsman et al. |
| 2015/0257749 A1 | 9/2015 | Denham et al. |
| 2015/0257750 A1 | 9/2015 | Kaiser et al. |
| 2015/0272586 A1* | 10/2015 | Herman ............ A61B 17/0401 606/139 |
| 2015/0342587 A1 | 12/2015 | Norton et al. |
| 2015/0342594 A1 | 12/2015 | Stone |
| 2015/0342595 A1 | 12/2015 | Norton |
| 2015/0354751 A1 | 12/2015 | Slagle et al. |
| 2016/0000483 A1 | 1/2016 | Stone |
| 2016/0022261 A1 | 1/2016 | Stone et al. |
| 2016/0038131 A1 | 2/2016 | White et al. |
| 2016/0058436 A1 | 3/2016 | Stone et al. |
| 2016/0081789 A1 | 3/2016 | Denham et al. |
| 2016/0089130 A1 | 3/2016 | Hoeppner et al. |
| 2016/0089138 A1 | 3/2016 | Early et al. |
| 2016/0106414 A1 | 4/2016 | Stone et al. |
| 2016/0113691 A1 | 4/2016 | Fritzinger et al. |
| 2016/0128683 A1 | 5/2016 | Denham et al. |
| 2016/0128684 A1 | 5/2016 | Stone et al. |
| 2016/0183935 A1 | 6/2016 | Stone |
| 2016/0199053 A1 | 7/2016 | Norton et al. |
| 2016/0199115 A1 | 7/2016 | Anderson et al. |
| 2016/0206307 A1 | 7/2016 | Wack et al. |
| 2016/0213369 A1 | 7/2016 | Stone et al. |
| 2016/0213480 A1 | 7/2016 | Stone et al. |
| 2016/0242760 A1 | 8/2016 | Kaiser et al. |
| 2016/0242793 A1 | 8/2016 | Norton et al. |
| 2016/0270822 A1 | 9/2016 | Cresina et al. |
| 2016/0270923 A1 | 9/2016 | Finley et al. |
| 2016/0287242 A1 | 10/2016 | Troxel et al. |
| 2016/0310128 A1 | 10/2016 | Denham |
| 2016/0310129 A1 | 10/2016 | Hoeppner et al. |
| 2016/0310186 A1 | 10/2016 | Hoeppner et al. |
| 2016/0361073 A1 | 12/2016 | Heilman et al. |
| 2017/0014225 A1 | 1/2017 | Denham et al. |
| 2017/0020507 A1 | 1/2017 | Denham et al. |
| 2017/0035411 A1 | 2/2017 | Kaiser et al. |
| 2017/0049557 A1 | 2/2017 | Denham et al. |
| 2017/0065278 A1 | 3/2017 | Stone et al. |
| 2017/0071595 A1 | 3/2017 | Stone et al. |
| 2017/0079799 A1 | 3/2017 | Smith et al. |
| 2017/0086816 A1 | 3/2017 | Norton |
| 2017/0119382 A1 | 5/2017 | Denham et al. |
| 2017/0128215 A1 | 5/2017 | Denham |
| 2017/0151054 A1 | 6/2017 | Stone et al. |
| 2017/0172561 A1 | 6/2017 | Denham |
| 2017/0172604 A1 | 6/2017 | Denham |
| 2017/0181746 A1 | 6/2017 | Denham et al. |
| 2017/0189011 A1 | 7/2017 | Stone et al. |
| 2017/0202587 A1 | 7/2017 | Stone et al. |
| 2017/0215876 A1 | 8/2017 | Norton et al. |
| 2017/0266014 A1 | 9/2017 | Stone et al. |
| 2017/0273686 A1 | 9/2017 | Denham et al. |
| 2017/0290579 A1 | 10/2017 | Norton |
| 2017/0311947 A1 | 11/2017 | Kaiser et al. |
| 2017/0319195 A1 | 11/2017 | Denham et al. |
| 2017/0319204 A1 | 11/2017 | Norton et al. |
| 2017/0325808 A1 | 11/2017 | Stone et al. |
| 2017/0333176 A1 | 11/2017 | Stone et al. |
| 2017/0354509 A1 | 12/2017 | Finley et al. |
| 2017/0360425 A1 | 12/2017 | Stone et al. |
| 2018/0000477 A1 | 1/2018 | Kaiser et al. |
| 2018/0014864 A1 | 1/2018 | Stone et al. |
| 2018/0021036 A1 | 1/2018 | Kaiser et al. |
| 2018/0021125 A1 | 1/2018 | Berelsman et al. |
| 2018/0042609 A1 | 2/2018 | Denham et al. |
| 2018/0085119 A1 | 3/2018 | Stone et al. |
| 2018/0125475 A1 | 5/2018 | Lozier et al. |
| 2018/0125476 A1 | 5/2018 | Kaiser et al. |
| 2018/0125477 A1 | 5/2018 | Stone |
| 2018/0132871 A1 | 5/2018 | Heilman et al. |
| 2018/0153538 A1 | 6/2018 | Kaiser et al. |
| 2018/0153565 A1 | 6/2018 | Stone et al. |
| 2018/0161030 A1 | 6/2018 | Stone et al. |
| 2018/0177501 A1 | 6/2018 | Kaiser et al. |
| 2018/0193015 A1 | 7/2018 | Denham et al. |
| 2018/0221017 A1 | 8/2018 | Stone et al. |
| 2018/0235595 A1 | 8/2018 | Palese et al. |
| 2018/0235597 A1 | 8/2018 | Troxel et al. |
| 2018/0235747 A1 | 8/2018 | Berelsman et al. |
| 2018/0249997 A1 | 9/2018 | Stone et al. |
| 2018/0256152 A1 | 9/2018 | Palese et al. |
| 2018/0256153 A1 | 9/2018 | Stone et al. |
| 2018/0338755 A1 | 11/2018 | Palese et al. |
| 2019/0046185 A1 | 2/2019 | Norton et al. |
| 2019/0083233 A1 | 3/2019 | Denham et al. |
| 2019/0150909 A1 | 5/2019 | Stone et al. |
| 2019/0150923 A1 | 5/2019 | Stone et al. |
| 2019/0159772 A1 | 5/2019 | Norton et al. |
| 2019/0231348 A1 | 8/2019 | Stone et al. |
| 2019/0231371 A1 | 8/2019 | Maxson et al. |
| 2019/0254652 A1 | 8/2019 | Stone et al. |
| 2019/0274681 A1 | 9/2019 | Denham et al. |
| 2019/0282227 A1 | 9/2019 | Norton |
| 2019/0290258 A1 | 9/2019 | Denham et al. |
| 2019/0298345 A1 | 10/2019 | Denham et al. |
| 2019/0328382 A1 | 10/2019 | Stone et al. |
| 2019/0350577 A1 | 11/2019 | Norton et al. |
| 2019/0365376 A1 | 12/2019 | Stone et al. |
| 2020/0029955 A1 | 1/2020 | Stone et al. |
| 2020/0069304 A1 | 3/2020 | Norton |
| 2020/0085562 A1 | 3/2020 | Stone et al. |
| 2020/0107937 A1 | 4/2020 | Denham et al. |
| 2020/0129214 A1 | 4/2020 | Pepper et al. |
| 2020/0178959 A1 | 6/2020 | Denham et al. |
| 2020/0187932 A1 | 6/2020 | Kaiser et al. |
| 2020/0187933 A1 | 6/2020 | Kaiser et al. |
| 2020/0188003 A1 | 6/2020 | Schlotterback et al. |
| 2020/0197002 A1 | 6/2020 | Stone et al. |
| 2020/0222042 A1 | 7/2020 | Berelsman et al. |
| 2020/0281637 A1 | 9/2020 | Denham |
| 2020/0297338 A1 | 9/2020 | Stone et al. |
| 2020/0337697 A1 | 10/2020 | Norton et al. |
| 2020/0367880 A1 | 11/2020 | Stone et al. |
| 2021/0038233 A1 | 2/2021 | Heilman et al. |

(56) References Cited

U.S. PATENT DOCUMENTS

| | | |
|---|---|---|
| 2021/0077131 A1 | 3/2021 | Denham et al. |
| 2021/0106322 A1 | 4/2021 | Hoeppner et al. |
| 2021/0121171 A1 | 4/2021 | Palese et al. |
| 2021/0137514 A1 | 5/2021 | Lawhorn et al. |
| 2021/0177397 A1 | 6/2021 | Stone et al. |
| 2021/0228203 A1 | 7/2021 | Denham et al. |
| 2021/0244443 A1 | 8/2021 | Coyne et al. |
| 2021/0290250 A1 | 9/2021 | Denham et al. |
| 2021/0315555 A1 | 10/2021 | Denham et al. |
| 2021/0315656 A1 | 10/2021 | Denham et al. |
| 2021/0315657 A1 | 10/2021 | Denham et al. |
| 2021/0330311 A1 | 10/2021 | Denham et al. |
| 2021/0361286 A1 | 11/2021 | Stone et al. |
| 2021/0401477 A1 | 12/2021 | Weiner et al. |
| 2022/0054123 A1 | 2/2022 | Kaiser et al. |
| 2022/0061861 A1 | 3/2022 | Coyne et al. |
| 2022/0087672 A1 | 3/2022 | Norton |

OTHER PUBLICATIONS

File History for U.S. Serial No. PCT/US17/35792 as accessed from U.S. Patent and Trademark Office.

File History for U.S. Appl. No. 62/344,489 as accessed from U.S. Patent and Trademark Office.

File History for U.S. Appl. No. 62/368,023 as accessed from U.S. Patent and Trademark Office.

\* cited by examiner

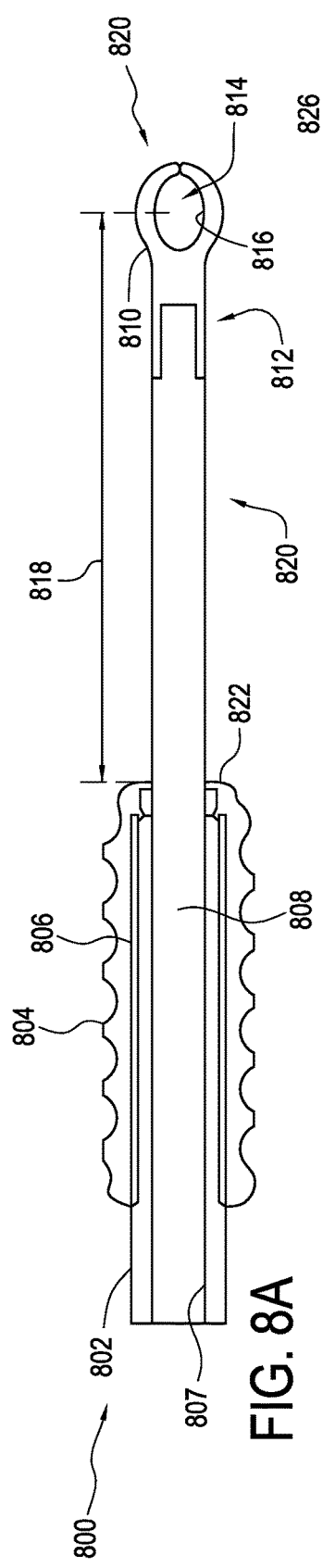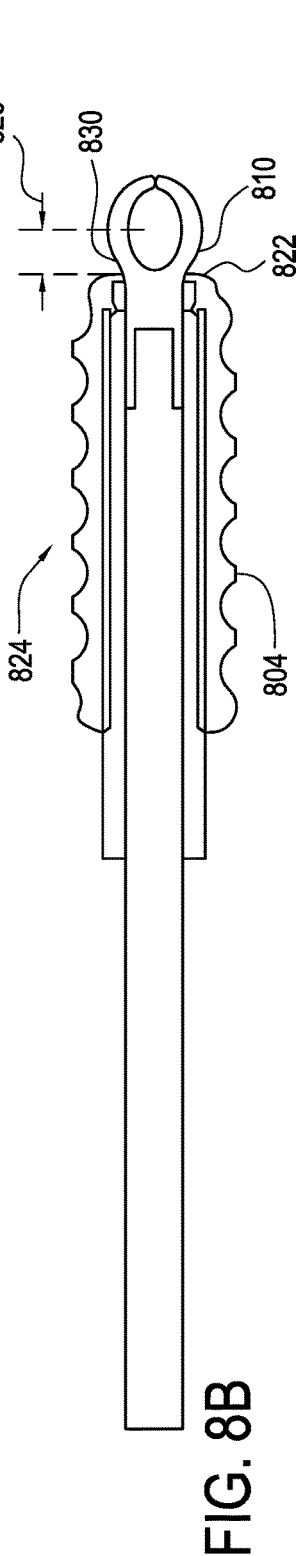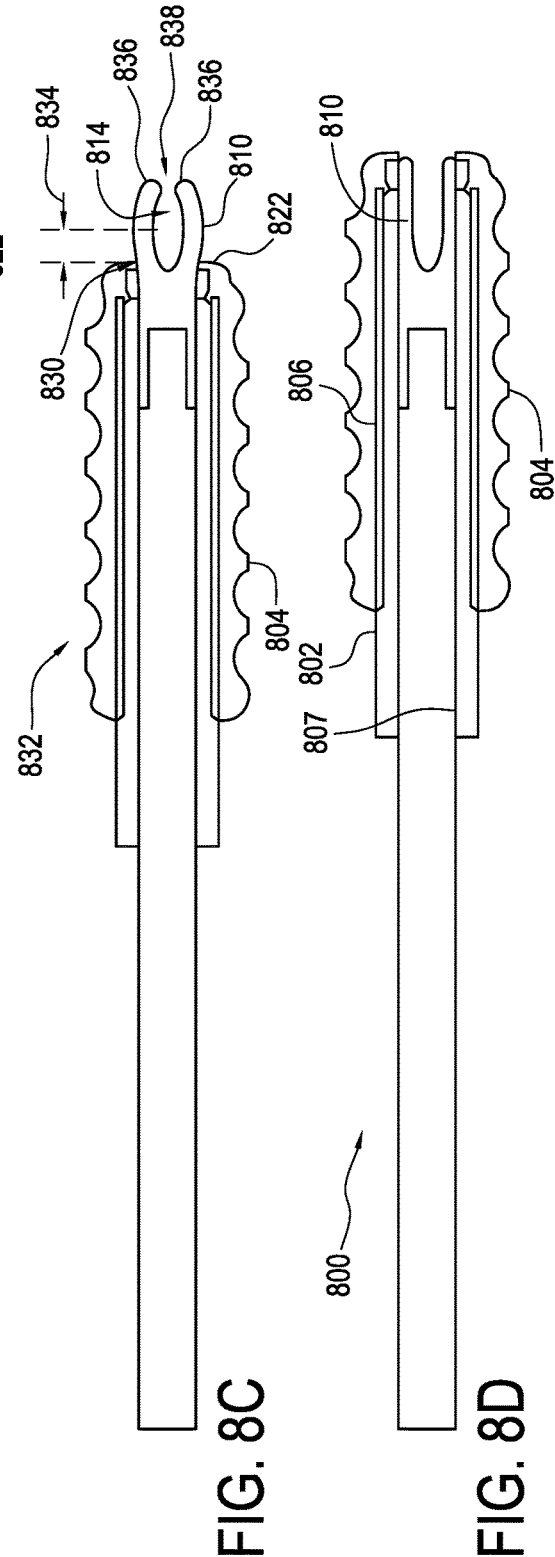
FIG. 8A  FIG. 8B  FIG. 8C  FIG. 8D

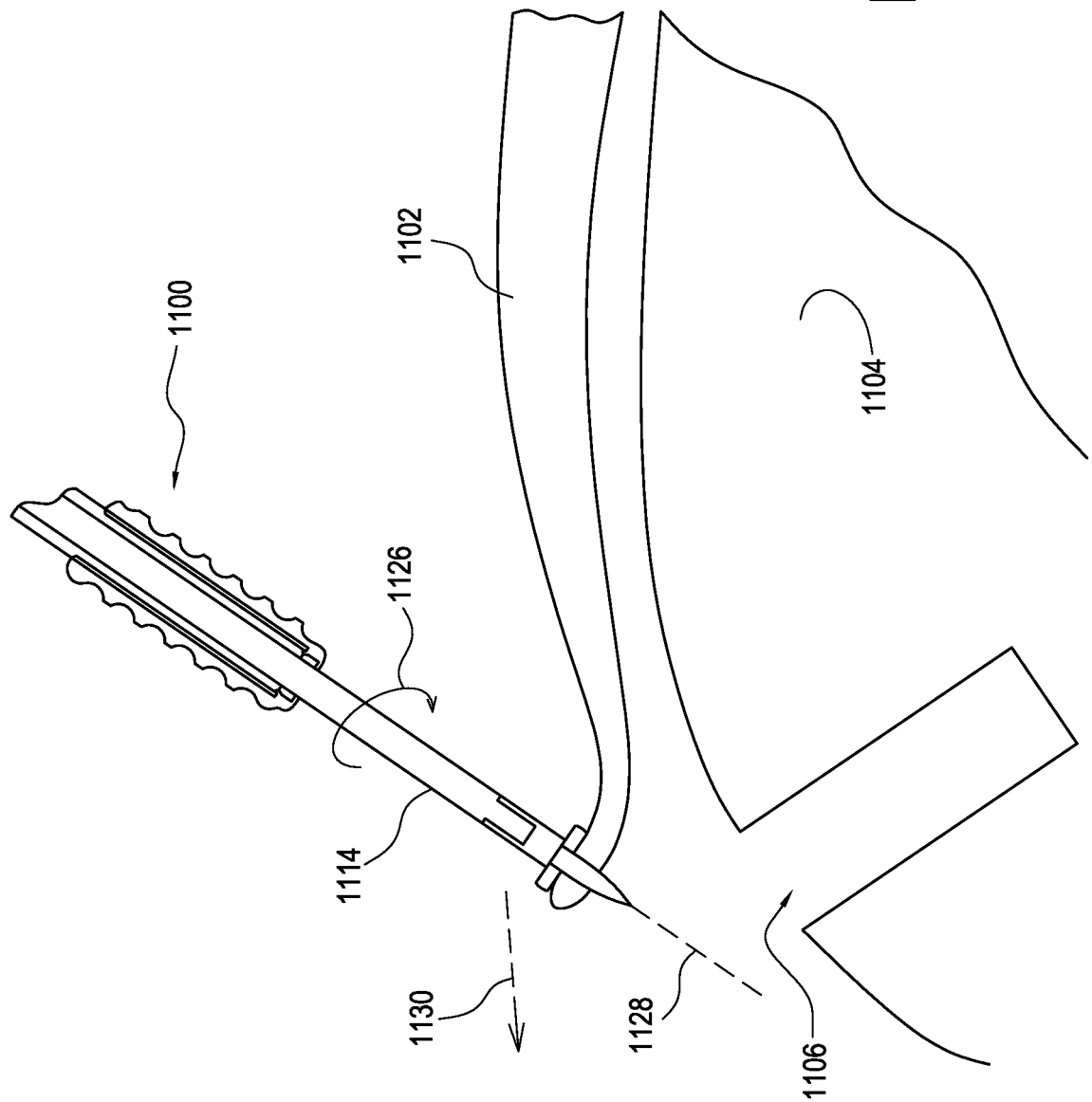

SUTURE TOOL AND METHOD OF USE

CROSS-REFERENCE TO RELATED APPLICATIONS

The present application is a continuation of U.S. patent application Ser. No. 16/206,736 filed on Nov. 30, 2018, which in turn is a continuation of international patent application number PCT/US2017/035792 having an international filing date of Jun. 2, 2017 which in turn claims the benefit of U.S. provisional patent application No. 62/344,489 filed on Jun. 2, 2016, and claims the benefit of U.S. provisional patent application No. 62/368,023 filed on Jul. 28, 2016, the disclosures of all of the foregoing are incorporated herein by reference in their entirety.

FIELD OF THE INVENTION

The present invention relates to a system, method and apparatus for fixturing tissue and more specifically to adjustable tissue fixturing.

SUMMARY

A wide variety of traumatic injuries can result in detachment of ligament from bone. In such circumstances surgical reattachment and, in particular, arthroscopic reattachment offers the potential of substantial recovery. Factors that bear strongly on successful reattachment include accurate positioning of the ligament tissue with respect to the underlying bone, and the presence of appropriate tension in the suture material maintaining this positioning.

Achieving these parameters in practice is difficult. Once the tissue has been attached to the suture, a distal end of the suture must be positioned so as to properly locate the ligament tissue with respect to the bone. Thereafter, a fixturing mechanism must be applied to ensure that this relationship is maintained. The process must account for the fact that application of the fixturing mechanism may tend to change the position and/or tension of a portion of the suture material.

The present invention includes an integrated surgical tool including an anchor driver and a guide portion. The guide portion is arranged to allow a user to position first and second materials (e.g. bone, soft tissue or synthetic tissue or device) in relation to one another and then release the anchor driver so as to allow engagement of the anchor driver with one or more of the tissues and fixate the tissues together (e.g. ligament or tendon to bone). Depending on the particular arrangement of the surgical tool, the surgical tool will include a suture guide that positions a suture within a prepared bore of a substrate bone material. The suture, having been attached to a soft tissue or material, is then fixed in place with respect to the bone by releasing the anchor driver portion and allowing a bone anchor coupled to the anchor driver to be fully engaged with the substrate bone material.

In other embodiments, for example, soft tissue will be directly positioned and held in place by a guide portion of the surgical tool. Once the soft tissue is positioned, an anchor guide is released and the anchor (anchor, suture anchor, soft tissue anchor, threaded device or driven in device) engages both the soft tissue and underlying bone tissue to achieve effective fixation of the two materials.

In sum, in certain embodiments, the invention includes a surgical tool that incorporates a suture guide and anchor driver supporting an anchor where the anchor is maintained at a distance from the suture guide until release of a detent mechanism. Thereafter, the anchor is allowed to move into proximity to the suture guide, fixing a suture supported by the suture guide to a substrate, the entire procedure being achievable with a single hand. In certain embodiments, the invention includes a surgical tool comprising, a handle portion, said handle portion including a detent mechanism, a tissue positioning portion, said tissue positioning portion being releasably coupled to said handle portion through said detent mechanism; and a substrate anchor driver portion, said substrate anchor driver portion including a coupling feature for coupling said substrate anchor driver portion to a substrate anchor, wherein said handle portion, said tissue positioning portion and said substrate anchor driver portion share a mutual longitudinal axis, and wherein said tissue positioning portion and said substrate anchor driver portion are disposed in controlled sliding relation to one another, subject to operation of said detent mechanism.

The following description is provided to enable any person skilled in the art to make and use the disclosed inventions and sets forth the best modes presently contemplated by the inventors of carrying out their inventions. In the following description, for purposes of explanation, numerous specific details are set forth in order to provide a thorough understanding of the present invention. It will be apparent, however, to one skilled in the art, that the present invention may be practiced without these specific details. In other instances, well-known structures and devices are shown in block diagram form in order to avoid unnecessarily obscuring the substance disclosed. These and other advantages and features of the invention will be more readily understood in relation to the following detailed description of the invention, which is provided in conjunction with the accompanying drawings.

It should be noted that, while the various figures show respective aspects of the invention, no one figure is intended to show the entire invention. Rather, the figures together illustrate the invention in its various aspects and principles. As such, it should not be presumed that any particular figure is exclusively related to a discrete aspect or species of the invention. To the contrary, one of skill in the art would appreciate that the figures taken together reflect various embodiments exemplifying the invention.

Correspondingly, referenced throughout the specification to "one embodiment" or "an embodiment" means that a particular feature, structure, or characteristic described in connection with the embodiment is included in at least one embodiment of the present invention. Thus, the appearance of the phrases "in one embodiment" or "in an embodiment" in various places throughout the specification are not necessarily all referring to the same embodiment. Furthermore, the particular features, structures, or characteristics may be combined in any suitable manner in one or more embodiments.

BRIEF DESCRIPTION OF THE DRAWINGS

FIGS. 8A-8D shows, in schematic cross-section, a portion of a surgical tool prepared according to principles of the invention;

FIGS. 11A-11H show, in schematic cross-sectional view, various states in an exemplary method of using a surgical tool;

DETAILED DESCRIPTION

Figure 1:
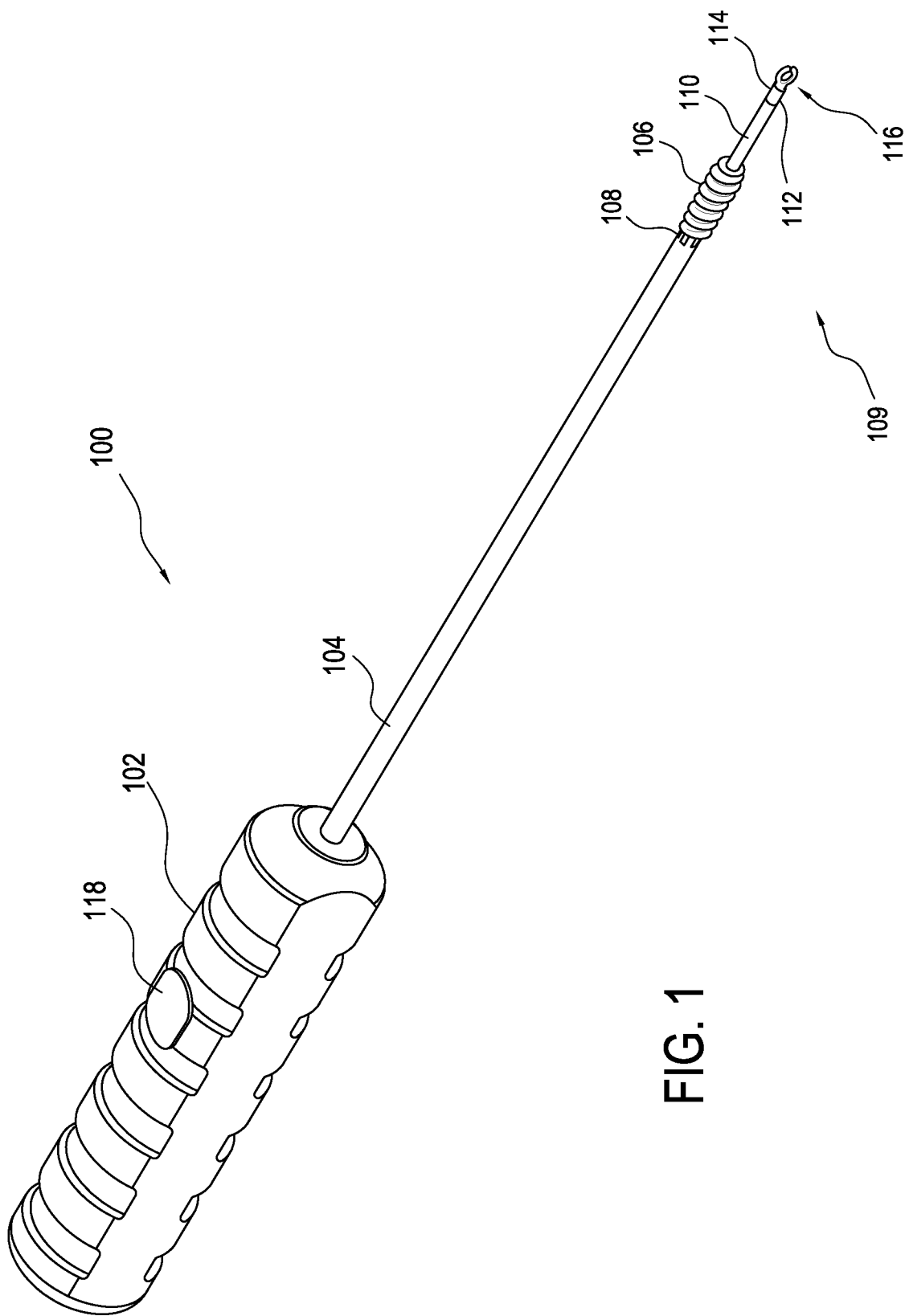
FIG. 1 shows an exemplary surgical tool according to principles of the invention.

The following description is provided to enable any person skilled in the art to make and use the disclosed inventions and sets forth the best modes presently contemplated by the inventors for carrying out their inventions. In the following description, for purposes of explanation, numerous specific details are set forth in order to provide a thorough understanding of the present invention. It will be apparent, however, to one skilled in the art that the present invention may be practiced without these specific details. In other instances, well-known structures and devices are shown in block diagram form in order to avoid unnecessarily obscuring the substance disclosed.

As noted above, the results of surgery directed to reattaching soft tissue and bone are likely to be improved by increasing the accuracy of relative tissue positioning, and effectively maintaining this position once established. Moreover, to the extent that this work can be completed by a single surgeon using two hands, efficiency and effectiveness are likely to be improved. As further described below, the present inventors have developed new and useful apparatus and methods for achieving these and other benefits.

In a first phase of operation, a surgical tool prepared according to principles of the invention is arranged and configured to have a first portion which includes a bearing surface within a bore in a substrate osseous tissue. The bearing surface supports a portion of a suture in sliding relation. By adjusting tension on a first end of the same suture, the location of soft tissue previously coupled to a second end of the same suture can be adjusted.

Once a desirable relative configuration of tissues has been achieved, a second phase of operation of the surgical tool can be effected to drive a bone anchor into the bore, capturing a further region of the suture between the anchor and the osseous tissue and effectively fixing a spatial relationship between the soft and osseous tissues.

During the first phase of operation, the bearing surface is maintained relatively distal to the anchor, which has been preloaded on the apparatus. As the second phase of operation is entered, a detent is released allowing a separation between the bearing surface and the anchor to be reduced. The structural relationships of the apparatus, and its components, as they exist within these two phases of operation, will be further clarified in light of the following figures and description.

It should be noted that the present invention includes a surgical tool that allows single-handed deployment of a suture or interference fixed tissue. Thus, a surgeon using a single hand can insert a suture guide or captured tissue within a prepared bore in a substrate. Thereafter, without removing his or her hand from the handle of the surgical tool, the surgeon can release a detent such that an anchor having a helical thread, a barbed surface feature, a smooth surface for interference fit, or any other appropriate fixation feature, can be deployed to retain the suture and/or soft tissue at the bore. This single-handed operation offers unique benefits, allowing rapid and practical fixation of tissue with limited personnel and within the constraints of space limitations in proximity to the patient.

FIG. 1 shows, in schematic perspective view, a surgical tool 100 prepared according to principles of the invention. Surgical tool 100 includes a handle member 102, and a cannulated anchor driver 104 (i.e., a hollow cylindrical anchor driver). An exemplary anchor, 106 is shown as engaged with a spline coupling 108 at a distal end 109 of the cannulated anchor driver 104.

One of skill in the art will appreciate that in other embodiments of the invention, the anchor driver will not include any spline feature, but will include other features or arrangements for coupling to the anchor. Thus, in certain embodiments, the anchor driver and anchor will have complementary helical threads. In still other embodiments, the anchor driver and anchor will have substantially smooth surfaces retained adjacent to one another by an interference fit. In still other embodiments, an adhesive material will retain the anchor driver and anchor in temporary connection to one another.

A suture guide shaft 110 is disposed coaxially within a longitudinal bore of the anchor driver 104. A distal end 109 of the suture guide shaft 110 supports a suture guide 112. In the illustrated embodiment, the suture guide 112 includes an optional generally cylindrical portion 114 and a generally toroidal portion 116. As will be further discussed below, the generally toroidal portion 116 defines an inner circumference and a normal axis generally transverse to a longitudinal axis of the guide shaft 110.

One of skill in the art will understand that the toroidal shape of toroidal portion 116 will, in certain embodiments, include a generally circular toroid as illustrated. In addition, in other embodiments any other shape will be employed according to the requirements of a particular application. Thus, in certain embodiments, the toroidal portion will have a generally rectangular configuration; in other embodiments a square configuration; in other embodiments any other regular or irregular polygonal configuration; in other embodiments a generally elliptical configuration; in other embodiments a generally oval configuration. In other words, any shape of suture guide will be employed where desirable in light of all design considerations.

As will also be further discussed below, a longitudinal displacement of suture guide shaft 110 with respect to the cannulated anchor driver 104 is controlled, in part, by a suture guide release button 118.

Figure 2:
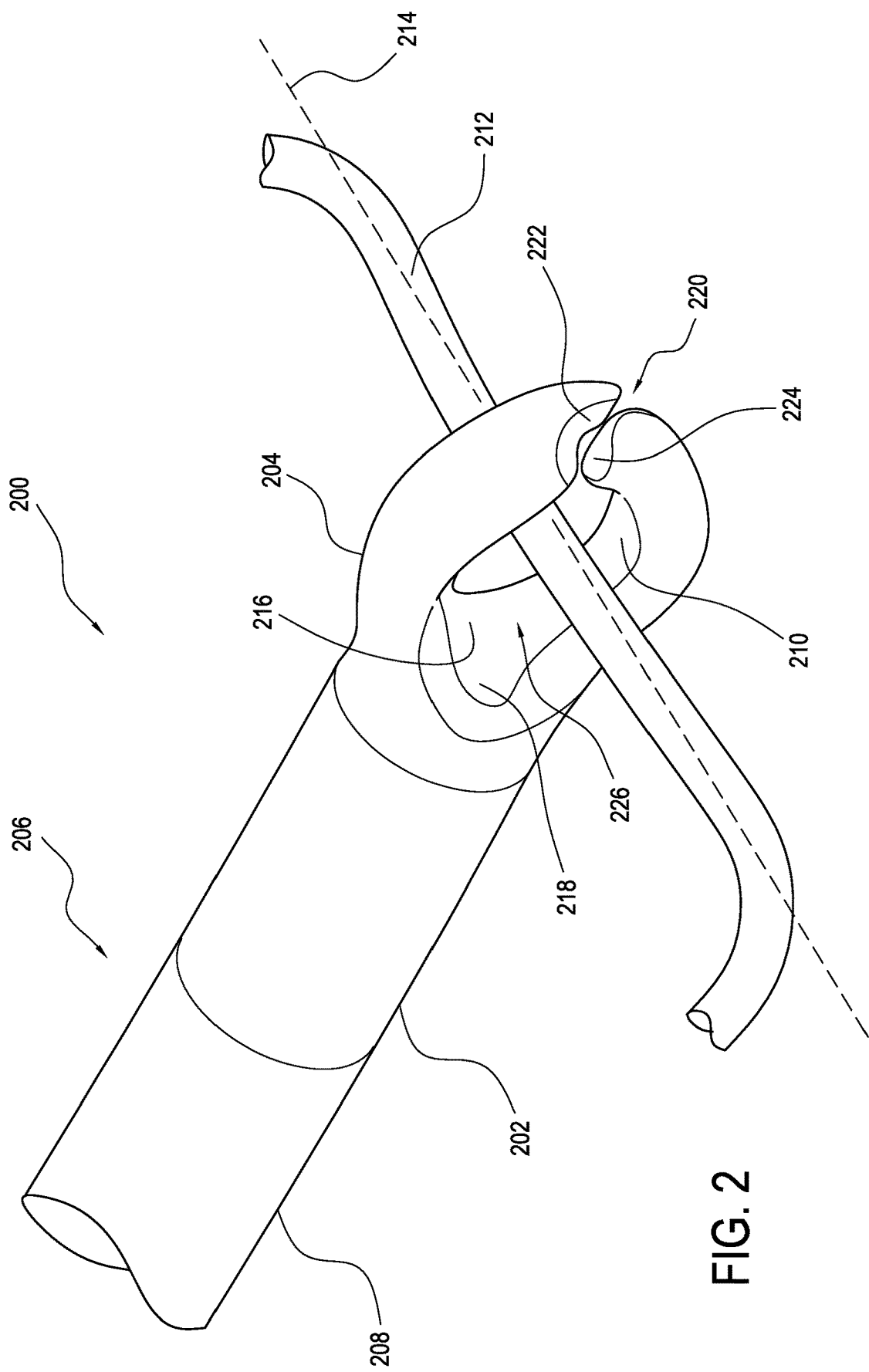
FIG. 2 shows, in schematic perspective view, certain further aspects of a suture guide according to principles of the invention.

FIG. 2 shows, in schematic perspective view, certain further aspects of a suture guide 200 of a novel surgical tool. The illustrated suture guide 200 includes a first generally cylindrical portion 202 and a second generally toroidal portion 204.

In certain embodiments, the generally cylindrical portion 202 is coupled to a distal end 206 of a suture guide shaft 208. This coupling may be affected by, for example and without limitation, threads, swaging, soldering, welding and/or an adhesive coupling. In other embodiments of the invention, the cylindrical portion 202 and the suture guide shaft 208 are integrally formed as a single structural member.

The generally toroidal portion 204 includes an internal bearing surface region 210. Bearing surface region 210 serves to support a portion of a suture 212 as illustrated. In various embodiments of the invention, surface region 210 will be more or less arcuate in form, defining (in certain embodiments) a saddle curve such that the surface region curve circumferentially around a generally circular axis of the toroidal portion, where the axis of the toroidal portion defines a plane generally perpendicular to a longitudinal axis of the suture 214, as depicted.

In certain embodiments of the invention, a proximal portion 216 of the internal surface region 210 includes a region of extended curvature 218. This region of extended curvature serves to support the suture 212 in sliding relation when the suture is disposed under additional tension so as to allow adjustment of the relative position of the soft and osseous tissues.

In certain embodiments of the invention, the generally toroidal portion 204 of the suture guide 200 embodies a slot 220 defined by first 222 and second 224 surface regions disposed in opposition to one another and generally transverse to the axis of the portal portion. One of skill in the art will appreciate that slot 220 allows the ready insertion of a suture portion 212 into the aperture 226 of the generally toroidal portion 204, thereby avoiding the need to thread the suture longitudinally through aperture 226, starting at a first end of the suture, and further allowing removal of the suture guide once the suture is fixed in place.

Figure 3:
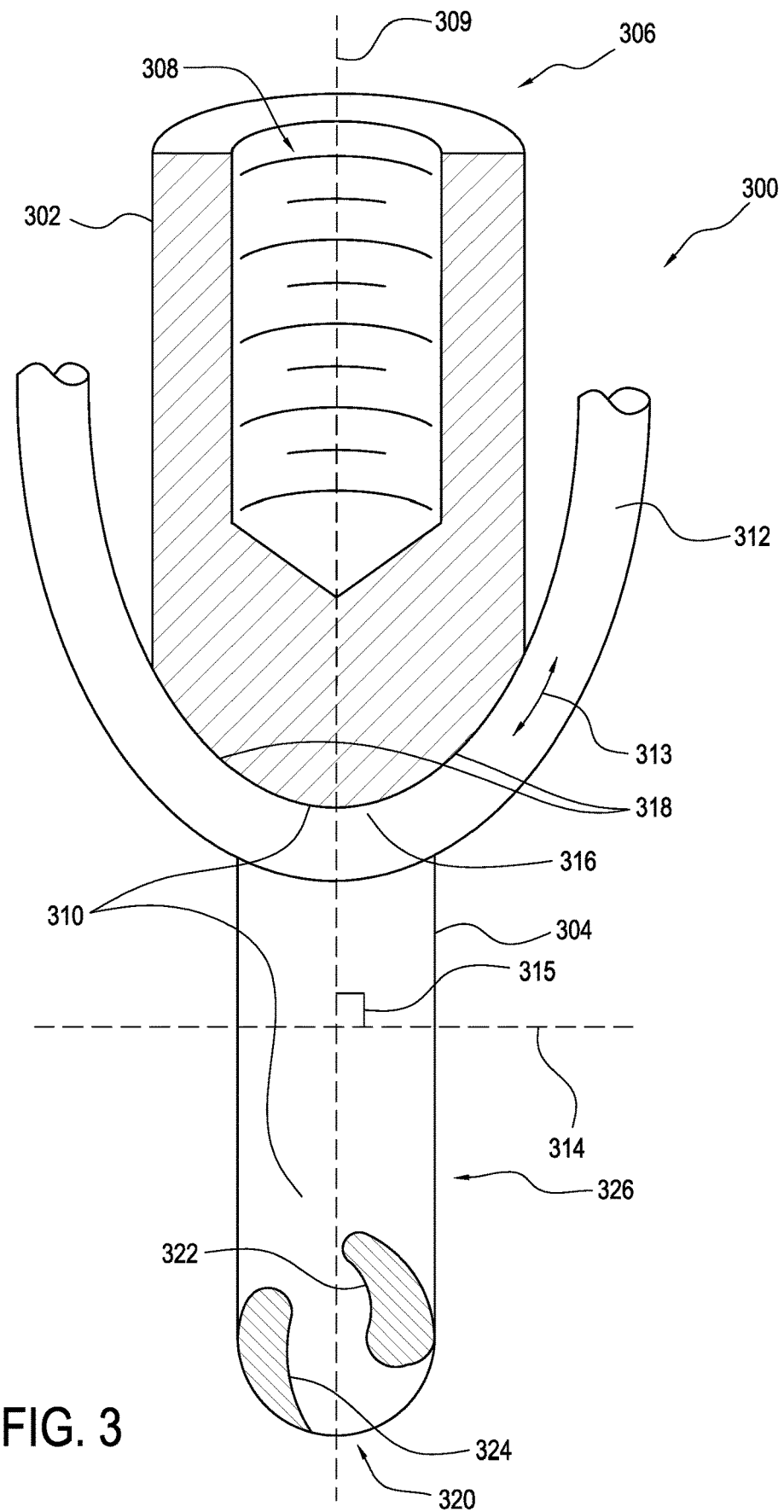
FIG. 3 shows, in schematic cross-section, further aspects of a suture guide prepared according to principles of the invention.

FIG. 3 shows, in schematic cross-section, further aspects of a suture guide 300 prepared according to principles of the invention. The illustrated suture guide includes a first generally cylindrical portion 302 and a second generally toroidal portion 304.

A proximal end 306 of the cylindrical portion 302 includes a generally circular cylindrical internally threaded bore 308. The generally circular cylindrical internally threaded bore 308 defines a longitudinal axis generally coincident with a longitudinal axis 309 of the first generally cylindrical portion 302.

The second generally toroidal portion 304 includes an internal bearing surface region 310 which serves to support a portion of a suture 312, as illustrated. An axis of rotation 314 of the generally toroidal portion 304 is, in the illustrated embodiment, disposed generally perpendicular 315 to the longitudinal axis 309 of the generally cylindrical portion 302.

In certain embodiments, a proximal region 316 of the internal surface region 310 includes a region of extended curvature 318. As discussed above, this region of extended curvature serves to support the suture 312 in sliding relation 313 when the suture is disposed under tension so as to allow adjustment of the relative position of the soft and osseous tissues.

In certain embodiments of the invention, the generally toroidal portion 304 of the suture guide embodies a slot 320. This slot 320 is defined by first 322 and second 324 surface regions disposed in opposition to one another and generally transverse to the axis of the portal portion. One of skill in the art will appreciate that slot 320 allows the ready insertion of a suture portion 312 into the aperture 326 of the generally toroidal portion 304. This precludes the need to thread the suture longitudinally through aperture 326, starting at a first end of the suture. Moreover, slot 320 allows removal of the suture guide once the suture is fixed in place by insertion of the bone anchor.

Figure 4A:
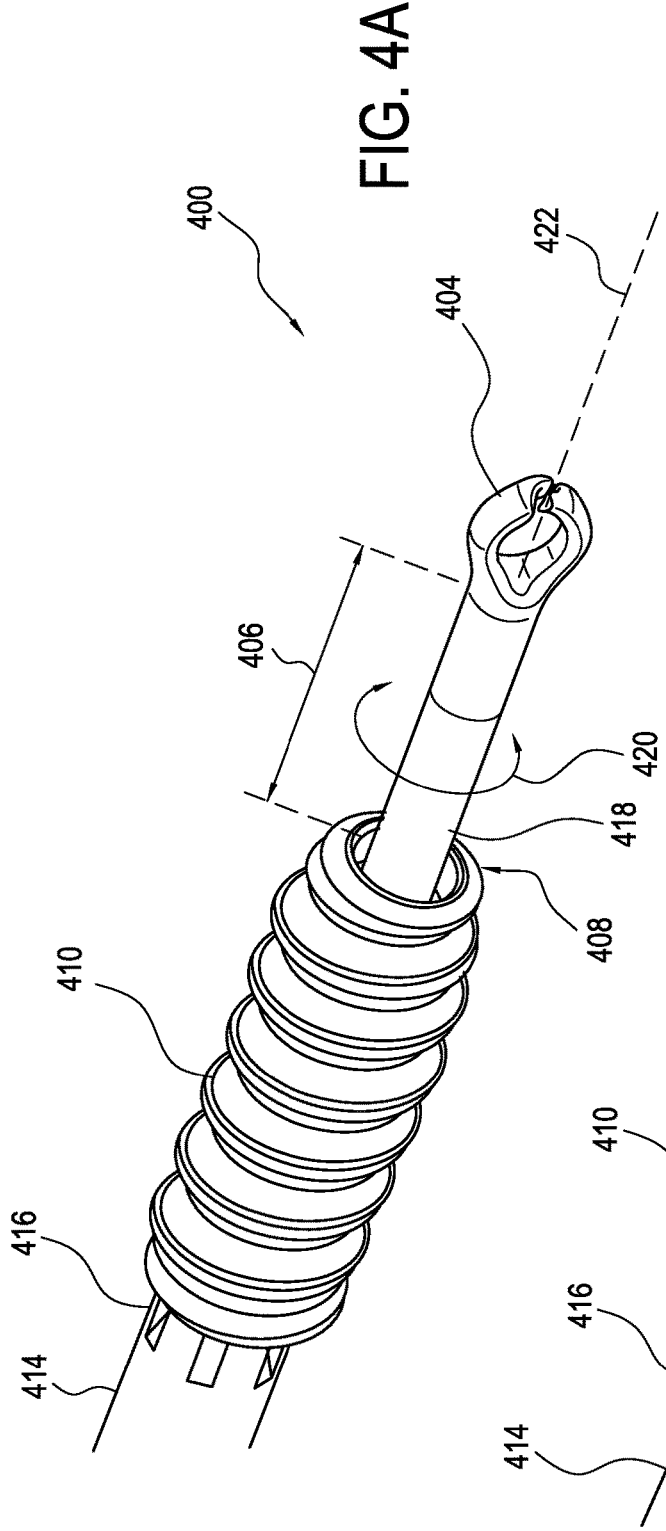
FIG. 4A shows, in schematic perspective view, a surgical tool prepared according to principles of the invention in an extended configuration.
Figure 4B:
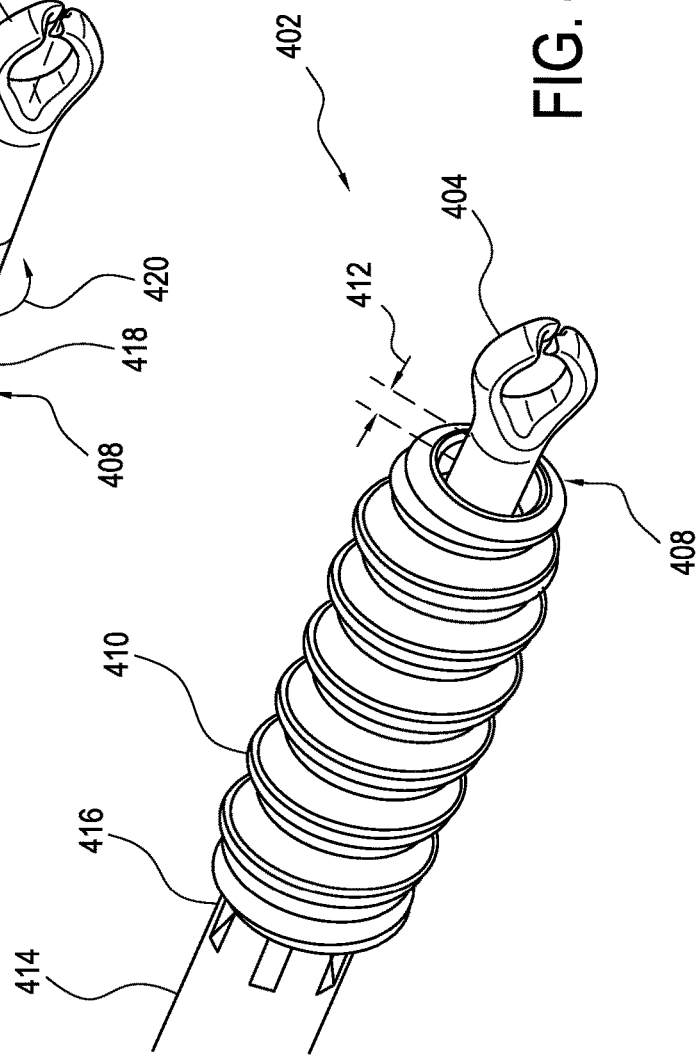
FIG. 4B shows, in schematic perspective view, a surgical tool prepared according to principles of the invention in a retracted configuration.

FIG. 4A and FIG. 4B show, in schematic perspective view, a surgical tool prepared according to principles of the invention. FIG. 4A shows the surgical tool in a first extended configuration 400 and FIG. 4B shows the surgical tool in a second retracted configuration 402. In extended configuration 400, a suture guide 404 is disposed at a first relatively large distance 406 from a distal end 408 of a bone anchor 410. In retracted configuration 402 the suture guide 404 is disposed at a second relatively small distance 412 from the distal end 408 of the bone anchor 410.

The bone anchor 410 is temporarily coupled to, and consequently maintained in a substantially fixed spatial relation to, a cannulated anchor driver 414. In the illustrated embodiment, the mechanism of this coupling includes a spline coupling between respective spline features, e.g. 416, of the cannulated anchor driver 414 and of the bone anchor 410.

In both configurations 400 and 402, of the illustrated embodiment, the suture guide 404 and a suture guide shaft 418 are substantially fixedly coupled to one another. In this configuration, the suture guide 404 and suture guide shaft 418 can be synchronously rotated 420 with respect to the cannulated anchor driver 414 about a longitudinal axis 422. It will be readily observed that the longitudinal axis 422 is substantially common to the suture guide shaft 418 and the cannulated anchor driver 414.

In certain embodiments of the invention, the detent mechanism is configured such that the suture guide shaft and anchor driver are rotationally fixed about their mutual longitudinal axis with respect to one another until the detent mechanism is activated. Thereafter, the suture anchor shaft is able to rotate about its longitudinal axis with respect to the anchor driver.

Figure 5A:
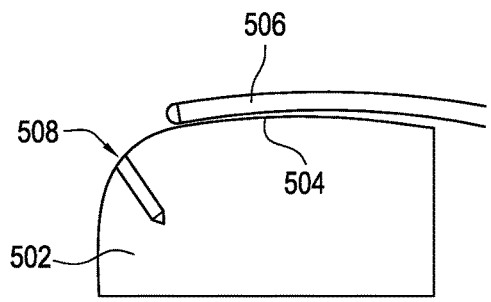
FIG. 5A-FIG. 5E illustrate selected states of an exemplary method of employing a surgical tool prepared according to principles of the invention.

FIG. 5A-FIG. 5E illustrate selected states of an exemplary method of employing a surgical tool prepared according to principles of the invention. FIG. 5A shows, in schematic form, a portion of a bone or other substrate medium 502. Adjacent a surface region 504 of the bone 502 is a portion of a detached ligament 506. In anticipation of reattachment of the ligament, a bore 508 has been drilled through surface region 504 and into the substrate bone 502.

Figure 5B:
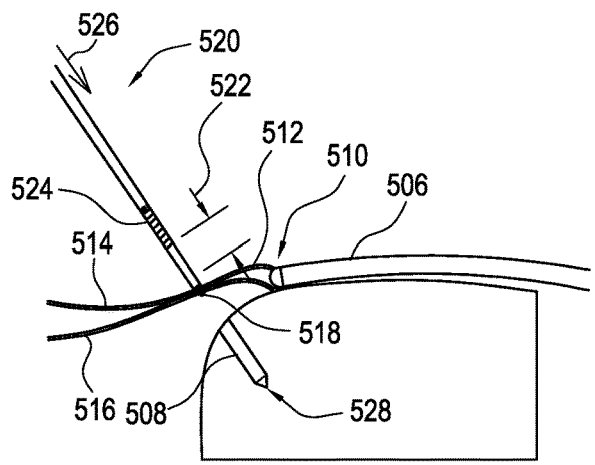

Referring to FIG. 5B, in preparation for reattachment, the ligament 506 is pierced 510 and a suture 512 is drawn through the ligament as shown. Two portions of the suture 514, 516 are disposed through an aperture (e.g., 326 of FIG. 3) of a suture guide 518, the suture guide being disposed at a distal end of a surgical tool 520.

As illustrated, the surgical tool 520 is configured in an extended configuration (consistent with the arrangement illustrated in FIG. 4A. Consequently a distance 522 between the suture guide 518 and a distal end of a bone anchor 524 is relatively long. Moreover, while the suture anchor is readily rotated about a longitudinal axis with respect to the bone anchor 524, distance 522 is substantially (though temporarily) fixed.

Consequently, applying a longitudinal force 526 to the surgical tool 520 tends to urge the suture guide 518 into the bore 508 and towards a distal end thereof 528.

Figure 5C:
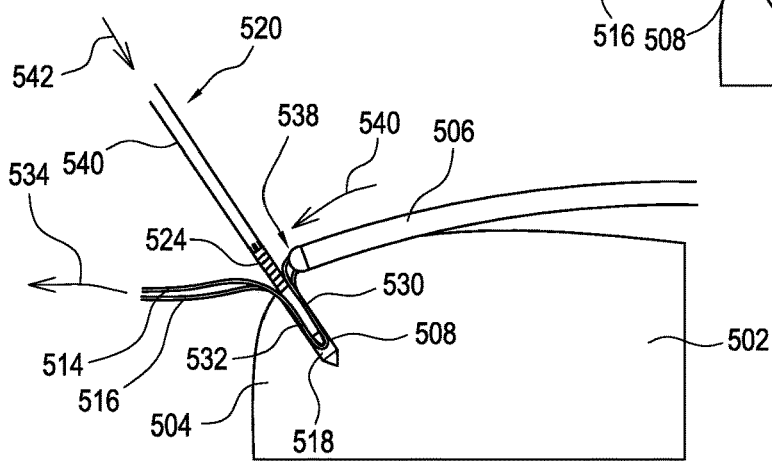

As illustrated in FIG. 5C, because the suture portions 514, 516 are disposed through the aperture of the suture guide 518, urging the suture guide 518 into bore 508 tends to draw corresponding regions 530, 532 of the suture into the bore 508. Concurrently, this motion of the surgical tool 520 brings the distal end of bone anchor 524 adjacent the surface region 504 of the bone at the mouth of the bore 508 where it passes through that surface region. By maintaining tension 534 on the suture portions 514, 516 on the side of the suture guide 518 opposite to the ligament 506, this motion can further cause a proximal end 538 of the ligament 506 to be displaced 540 towards the mouth of the bore.

By manipulation of tension 534 on the suture portions, and consequent adjustment of the position of the longitudinal suture with respect to the suture anchor, accurate and effective positioning of the ligament 506 with respect to the surface 504 of the bone 502 can be achieved. Moreover, this can be accomplished by a single individual using two hands.

That same individual, without assistance, can then press the release button (element 118, FIG. 1) and release the detent referred to in relation to that release button while concurrently rotating a handle of the surgical tool 520. Rotation of the handle, which is rotationally fixed with respect to the cannulated anchor driver 540, and therefore with respect to the bone anchor 524, causes a corresponding rotation of the bone anchor 524. By combining this rotational motion with an application of longitudinal force 542 external helical threads on the bone anchor 524 can be made to engage with the internal surface of bore 508 and thereby advance the bone anchor 524 into the bore 508.

One of skill in the art will appreciate that, while a bone anchor 524, exhibiting external helical threads is shown for illustrative purposes in FIGS. 5A-5E, other anchors known in the art, or that may become known in the art, may likewise be applied within the scope of the invention. Thus, for example, a barbed anchor, rather than a threaded anchor may be employed. In addition, an anchor may be employed that incorporates neither threads nor barbs, but is fixed within a bore by, for example, an interference fit. Likewise, an elastic retainer, an adhesively retained stopper, or any other retaining device appropriate to the particular circumstances will be applied and considered to be within the scope of the invention.

Figure 5D:
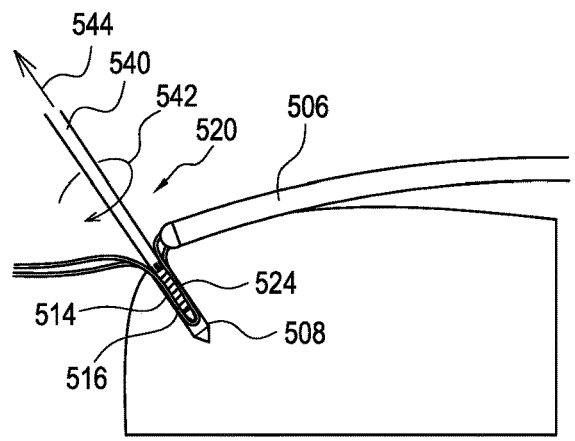

As illustrated in FIG. 5D, further rotation 542 of the cannulated anchor driver 540 causes the bone anchor 524 to be fully driven into the bore 508. This tends to trap the suture portions 514, 516 firmly against respective internal surface regions of the bore 508, thereby preventing displacement of the ligament 506. Once driving of the bone anchor 524 is complete, tension may be applied 544 to the surgical tool 520.

Figure 5E:
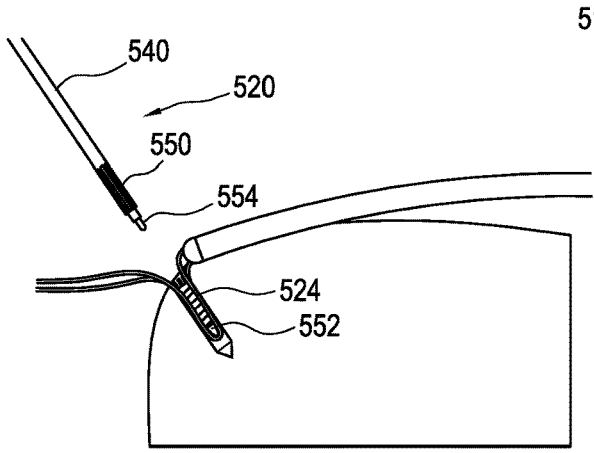

Referring to FIG. 5E, one sees that this tension results in the spline feature 550 of the cannulated anchor driver 540 disengage from the bone anchor 524 and allow the surgical tool 520 to be withdrawn. As the tool is withdrawn, a portion of the suture 552 previously disposed within the aperture 554 of the suture guide passes through a slot in the suture guide (as illustrated, for example, as element 220 of FIG. 2). This allows the suture guide to release the suture portion 552 and permits the withdrawal of the surgical tool 520 described above.

Figure 6:
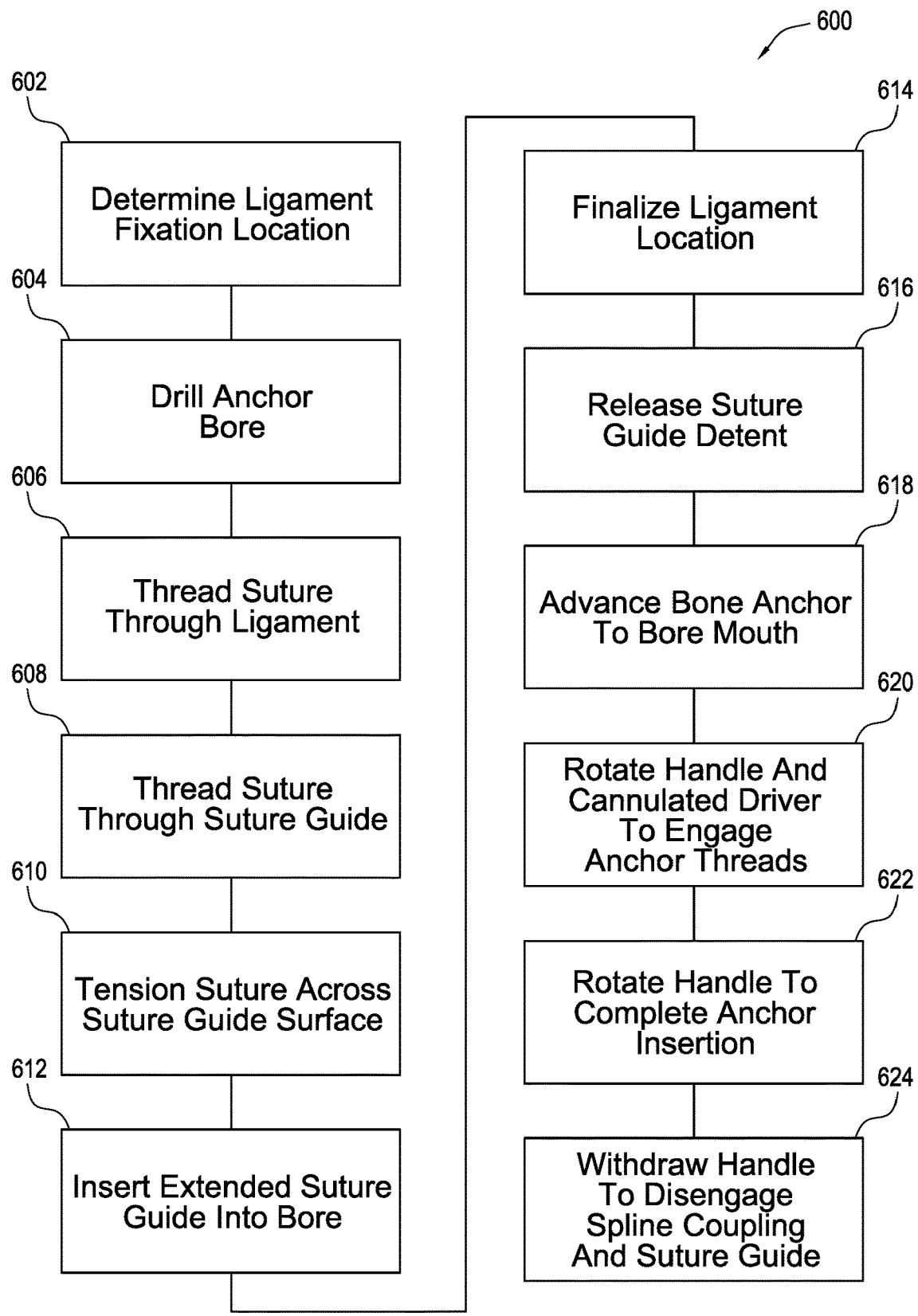
FIG. 6 shows, in flowchart form, certain portions of a method for using a surgical tool according to principles of the invention.

FIG. 6 shows, in flowchart form, certain portions of a method 600 for using a surgical tool according to principles of the invention. In the illustrated embodiment, the method includes determining a ligament fixation location 602 with respect to an underlying substrate such as bone and drilling an anchor bore in the bone 604 to receive a bone anchor and a length of suture. A length of suture is coupled to a ligament or other soft tissue by, for example, threading through the tissue with a needle 606. A portion of the suture is coupled to a suture guide by, for example, threading the suture through an aperture of a generally toroidal region the suture guide 608. The suture guide and suture are manipulated, with the application of appropriate pressure and tension (as would be understood by one of skill in the art) to insert the extended suture guide 612 into the bore drilled at step 604. Further application of pressure to the suture guide and tension on the suture, as well as direct manipulation of the soft tissue and underlying substrate allows finalization of the ligament location with respect to the bone 614.

While holding the suture in place, a release mechanism of the surgical tool is activated. This release mechanism releases a detent that couples the suture guide to a balance of the surgical tool 616. This release of the detent mechanism allows the surgical tool to advance a bone anchor supported by the surgical tool to be advanced 618 towards and into a mouth of the bore prepared at step 604. In certain embodiments of the invention, the bone anchor will contact the underlying bone and even be advanced by rotation or pressure into the bore before any release of the detent mechanism.

Rotation of a handle of the surgical tool conveys a torque through the handle, through an anchor driver, through a spline feature and into the bone anchor so that the bone anchor threads engage an internal surface region of the bore 620. Further rotation of the handle advances the bone anchor into the bore until the anchor is fully inserted at its destination 622.

Thereafter, the handle of the surgical tool is withdrawn, disengaging the spline coupling from the now-inserted bone anchor. As the surgical tool is withdrawn, the portion of the suture that was disposed within the suture guide passes through a slot in the suture guide 624. This allows complete withdrawal of the surgical tool and leaves the suture compressed and fixed to the internal surface of the bore by the inserted bone anchor.

Figure 7:
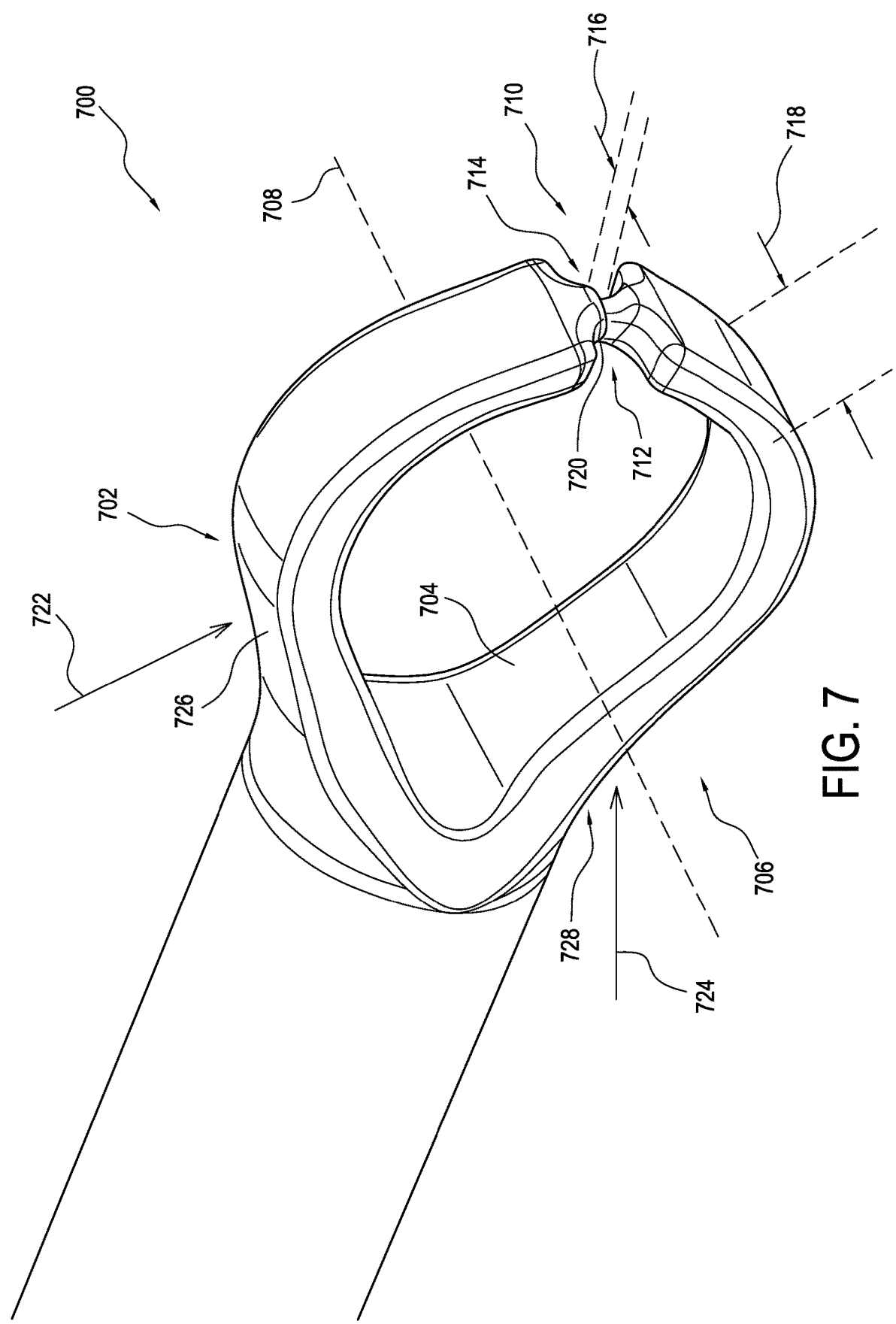
FIG. 7 shows, in schematic perspective view, a further suture guide for a surgical tool prepared according to principles of the invention.

FIG. 7 shows, in schematic perspective view, a further suture guide 700 for a surgical tool prepared according to principles of the invention. The suture guide 700 includes a generally toroidal portion 702 with an internal bearing surface region 704.

An internal circumferential bearing surface region 704 defines an aperture 706 about and transverse to an axis 708. As discussed above in relation to suture guide 200, the bearing surface region 704 serves to enclose a portion of a suture (not shown) disposed within and through aperture 706.

In contrast to suture guide 200, surface region 704 of suture guide 700 forms a contiguous surface region throughout 360° about axis 708. Whereas the corresponding surface region 210 of suture guide 200 is interrupted by slot 220, surface 704 of suture guide 700 is circumferentially continuous across region 710. Instead, and as illustrated, the suture guide is relieved 712, 714 in the vicinity of region 710 so that a dimension 716 of surface region 704 in the vicinity of 710 is relatively small in the direction of axis 708 as compared with a corresponding dimension elsewhere, e.g. 718, around the aperture 706.

The reduced internal circumferential surface region 720 will, in certain embodiments, include a frangible region, such that the application of certain forces, e.g. 722, 724, to corresponding external surface regions, e.g. 726, 728, results in a distortion of the cross-sectional shape of aperture 706 and, consequently, fracturing of the frangible portion to form an aperture in the vicinity of region 720. As will be further discussed below, the requisite forces 722, 724 will, in certain embodiments, be applied to surface regions 726, 728 respectively, by corresponding distal surface regions of a bone anchor.

It will be noted that, in contrast to the illustration of FIG. 2, the drawing of FIG. 7 embodies a plurality of polygonal regions. One of skill in the art will appreciate that this is merely a representational difference and that the suture guides illustrated are intended to be equivalent in terms of their defining curvatures. The actual curvature of the device, as prepared, may embody smooth curves, polygonal sections, and any combination thereof according to the particular circumstances to be addressed.

FIGS. 8A-8D shows, in schematic cross-section, a portion of a surgical tool 800 prepared according to principles of the invention. The surgical tool includes a cannulated anchor driver 802 temporarily slidingly coupled to a bone anchor 804 by complementary spline features 806 of the cannulated anchor driver 802 and bone anchor 804 respectively. Disposed within a cannula 807 of the cannulated anchor driver 802 is a portion of a suture guide shaft 808. A suture guide 810 is coupled to a distal end 812 of the suture guide shaft 808. In FIG. 8A surgical tool 800 is shown in an extended configuration 820 where the suture guide 810 is disposed at a first relatively large distance 818 from a distal end 822 of the bone anchor 804.

The suture guide 810 includes an aperture 814. As with the suture guide 700, an internal circumferential bearing surface region 816 is initially contiguous around the circumference of aperture 814. The surgical tool 800 is applied generally according to the method 600 described above with respect to FIG. 6.

FIG. 8B shows surgical tool 800 in a second intermediate configuration 824. In configuration 824, the suture guide 810 is disposed at a second relatively small distance 826 from distal end 822 of the bone anchor 804. In this configuration, distal end 822 of suture guide 804 is disposed in contact with an external circumferential surface region 830 of the suture guide 810.

FIG. 8C shows surgical tool 800 in a third intermediate configuration 832. In configuration 832, the suture guide 810 is disposed at a still smaller distance 834 from distal end 822 of the bone anchor 804. The reader will observe that interference between distal end 822 of the bone anchor has interfered with external surface region 830 of the suture guide 810. Consequently, the suture guide 810 has been distorted, elongating aperture 814, and causing a frangible region 836 of suture guide 810 to fracture. The resulting opening 838 of the suture guide aperture 814 allows the suture guide to be withdrawn from a portion of a suture captured by the suture anchor 804.

FIG. 8D shows surgical tool 800 in a fourth retracted configuration where the suture guide 810 is fully retracted within the cannula 807 of the cannulated anchor driver 802. Accordingly, the surgical tool 800 can be withdrawn from the suture anchor 804, disengaging the spline features 806 of the cannulated anchor driver 802 from the bone anchor 804, and leaving the bone anchor and suture secured in substrate bone.

In an alternative embodiment of the invention a suture guide is detachably coupled to a suture guide shaft. The suture guide may, for example, have a contiguous internal circumferential surface. Unlike the suture guide 810, the suture guide does not include a frangible portion. Rather, the suture guide is arranged and configured to be released from the suture guide shaft in response to an interference between the suture guide and a distal end 822 of the bone anchor, so that the suture guide is left behind in the bore when suture guide shaft is withdrawn. In order to achieve this, an interface between the suture guide and the suture guide shaft may be a smooth interference fit, or may include frangible features such as frangible threads, frangible barbs, frangible ribs, a frangible adhesive, or any other arrangement effective to achieve a temporary, but releasable coupling between the suture guide shaft and the suture guide.

In still another embodiment of the invention, the suture guide will pass into and through a bore in the anchor, but not through a cannula or bore of the anchor driver.

Figure 9:
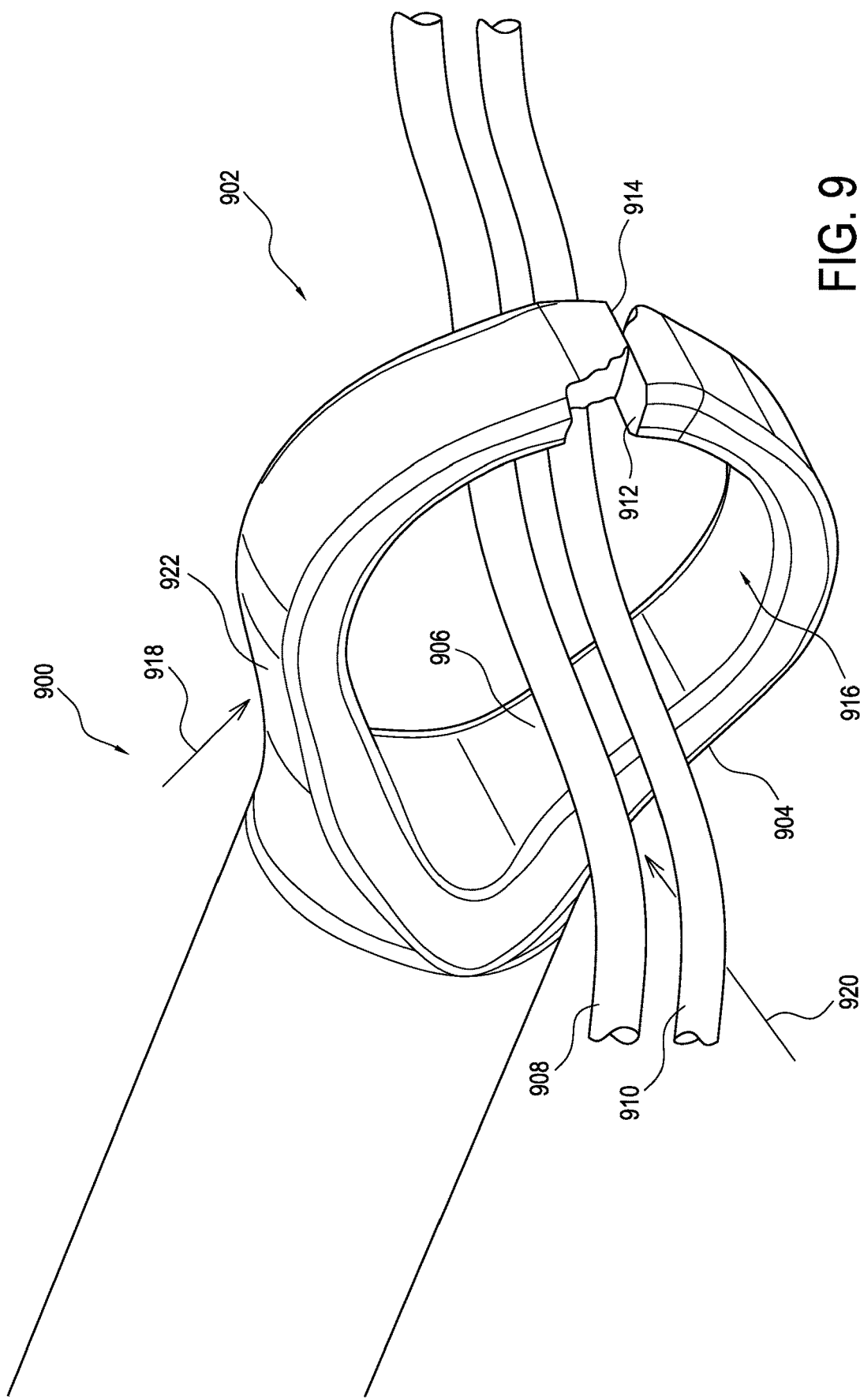
FIG. 9 shows, in cutaway perspective view, a portion of a further surgical tool prepared according to principles of the invention including a suture guide.

FIG. 9 shows, in cutaway perspective view, a portion of a further surgical tool 900 prepared according to principles of the invention including a suture guide 902. Suture guide 902 includes a generally toroidal portion 904 with an internal circumferential bearing surface 906. Internal circumferential bearing surface 906 serves to support a portion of a suture 908, 910 during, e.g., an arthroscopic surgery in the manner generally described above.

The toroidal portion 904 of suture guide 902 includes first 912 and second 914 generally radial internal surface regions. Surface regions 912 and 914 are initially disposed in generally parallel spaced relation to one another and either in contact with one another, or sufficiently proximate to one another to prevent egress of the suture portions 908, 910 from within an aperture 916 of the suture guide 902.

In the illustrated embodiment, the generally toroidal portion 904 of the suture guide 902 exhibits a geometry that, together with materials characteristic of the suture guide 902, serve to maintain surfaces 912 and 914 in proximity to one another when the suture guide 902 is in a relaxed state. However, when appropriate forces 918, 920 are applied to respective external surface regions, e.g., 922 of the suture guide 902, the suture guide tends to deform. This deformation tends to displace surfaces 912 and 914 away from one another, opening the suture guide and allowing it to be released from the suture portions 908 and 910.

In certain embodiments of the invention, the toroidal portion 904 of the suture guide 902 will include a generally elastic material having a spring characteristic that, along with the geometry of the suture guide 902, tends to maintain surfaces 912 and 914 in proximity to one another until the suture guide 902 is deformed. In such an embodiment, the deformation will be more or less elastic.

In other embodiments of the invention, the toroidal portion 904 of the suture guide 902 will include a generally inelastic malleable material having a characteristic that, along with the geometry of the suture guide 902, tends to maintain surfaces 912 and 914 in proximity to one another until the suture guide 902 is deformed. In such an embodiment, the deformation will be generally inelastic.

In certain further embodiments of the invention, the toroidal portion 904 of the suture guide will include a combination of elastic and/or malleable materials producing a desirable release characteristic of the suture portions when deformed. In still further embodiments of the invention, the toroidal portion of the suture guide will include a material such as a shape-memory alloy which will retain a first closed configuration of the suture guide while maintaining a first temperature, but which will assume a second open configuration of the suture guide as the suture guide achieves a second temperature. Thus, for example, a chilled suture guide will assume a closed configuration, but will tend to open as it warms to body temperature.

In still other embodiments of the invention, the suture guide will be detachable from the suture guide shaft such that, after insertion of the anchor, when the suture guide shaft is withdrawn, the suture guide is detached from the suture guide shaft and remains within the bore in the substrate underneath the anchor.

Figure 10A:
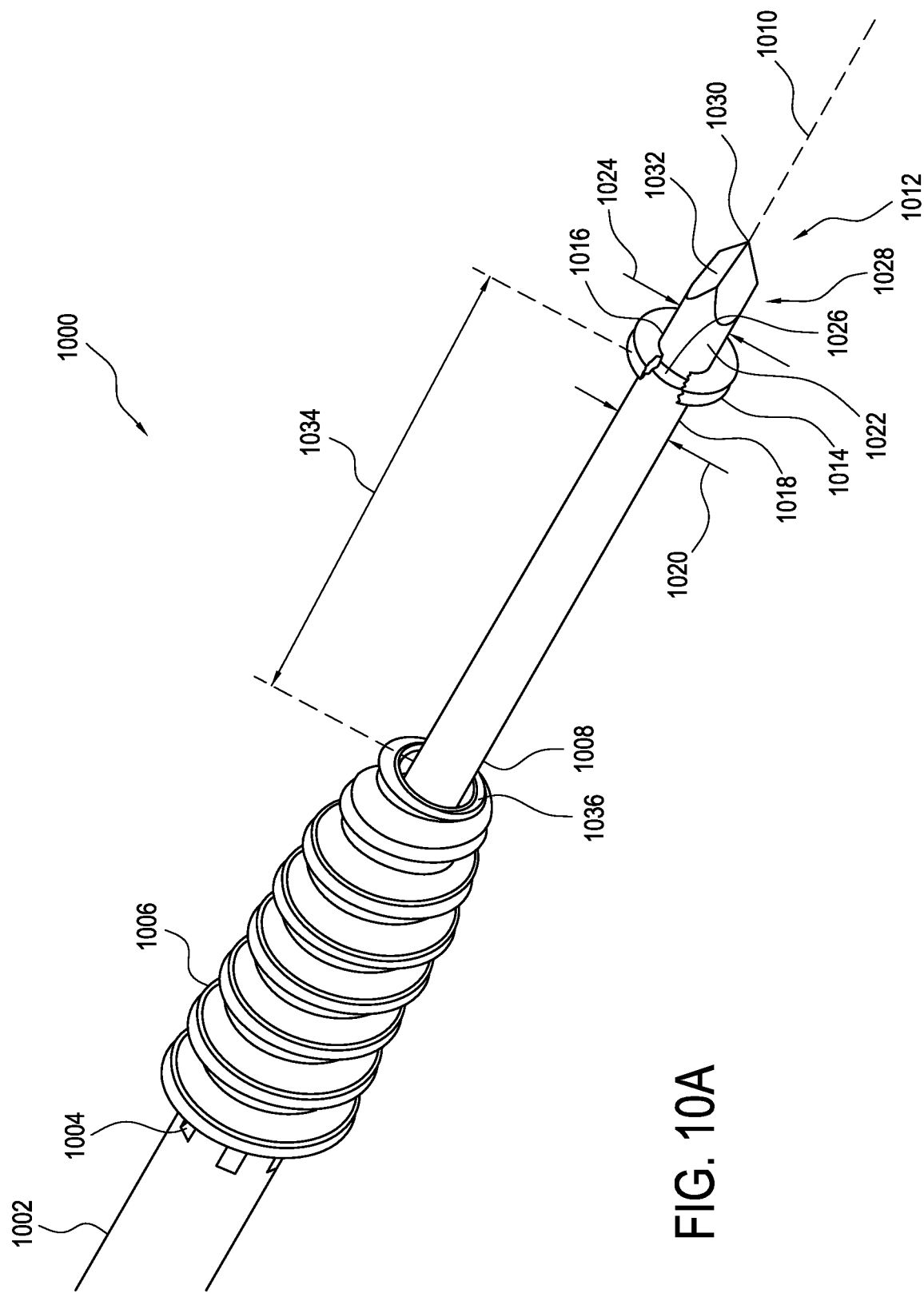
FIG. 10A shows, in cutaway perspective view, a further surgical tool prepared according to principles of the invention in an extended configuration.

FIG. 10A shows, in cutaway perspective view, a further surgical tool 1000 prepared according to principles of the invention. Like the various embodiments described above, exemplary surgical tool 1000 includes a cannulated anchor driver 1002 coupled through spline features 1004 to a bone anchor 1006. Disposed within and through a longitudinal cannula of the cannulated anchor driver 1002 and the bone anchor 1006 is a shaft 1008. The shaft 1008 defines a longitudinal axis 1010.

Near a distal end 1012 of the shaft 1008, a generally toroidal bearing washer 1014 is disposed coaxially about the shaft 1008. The generally toroidal bearing washer is supported on shaft 1008 by a snug but slidable interface 1016 between an internal circumferential surface of the washer 1014 and a corresponding external circumferential surface of the shaft 1008. In certain embodiments, a cross-section of the shaft 1008 is circular. It will be appreciated, however, by one of skill in the art, that in any of the embodiments disclosed in this application, other cross-sections are contemplated to be within the scope of the invention. Such other cross-sections will include, in various embodiments and without limitation, polygonal, elliptical and otherwise arcuate cross-sections.

A first relatively proximal circumferential surface region 1018 of the shaft 1008 has a relatively large diameter 1020. A second relatively distal circumferential surface region 1022 of the shaft 1018 has a relatively small diameter 1024. A generally radial surface region 1026 disposed between surface region 1018 and surface region 1022 defines a shoulder further supporting the washer 1014 and limiting its motion in a proximal direction along longitudinal axis 1010 by mechanical interference.

In the illustrated embodiment, a distal extremity 1028 of shaft 1008 tapers to a point 1030. This taper is defined by an intermediate surface region between circumferential surface region 1022 and point 1030.

In various respective embodiments, this intermediate surface region includes a substantially conical surface region, an elite-conical surface region (i.e. generally conical, but with a convex or concave surface curvature), a prismatic or pyramidal surface region including one or more generally flat surface regions (e.g., as shown 1032), and any combination thereof, to provide, respectively, piercing and cutting actions. In addition other modes of sharpening, such as and without limitation, chisel sharpening, will be employed in corresponding embodiments of the invention, according to the requirements of a particular application.

Figure 10B:
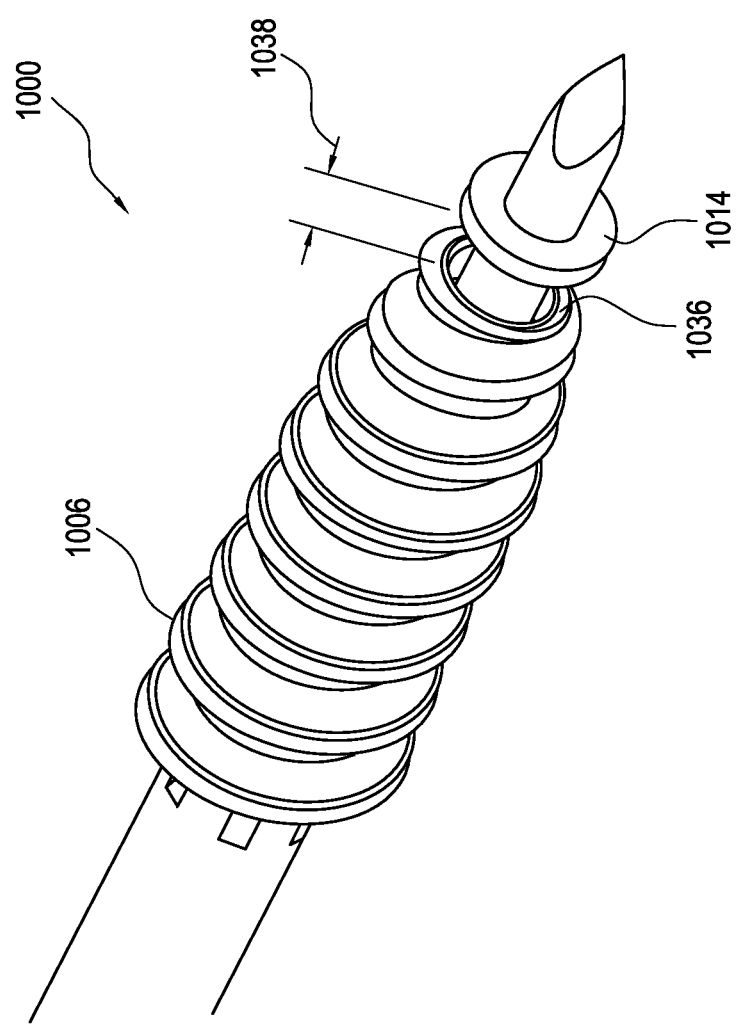
FIG. 10B shows, in schematic perspective view, a further surgical tool prepared according to principles of the invention in a retracted view.

In light of the foregoing disclosure, the reader will appreciate that the surgical tool 1000 is shown in an extended configuration such that distance 1034 between washer 1014 and a distal end 1036 of bone anchor 1006 is relatively long, as compared to the corresponding dimension of the same surgical tool when disposed in a retracted configuration. Such a retracted configuration is illustrated in FIG. 10B. As drawn, where the surgical tool 1000 is in its retracted configuration, washer 1014 is disposed relatively proximate to distal end 1036 of bone anchor 1006 and distance 1038 is consequently relatively short.

Figure 11A:
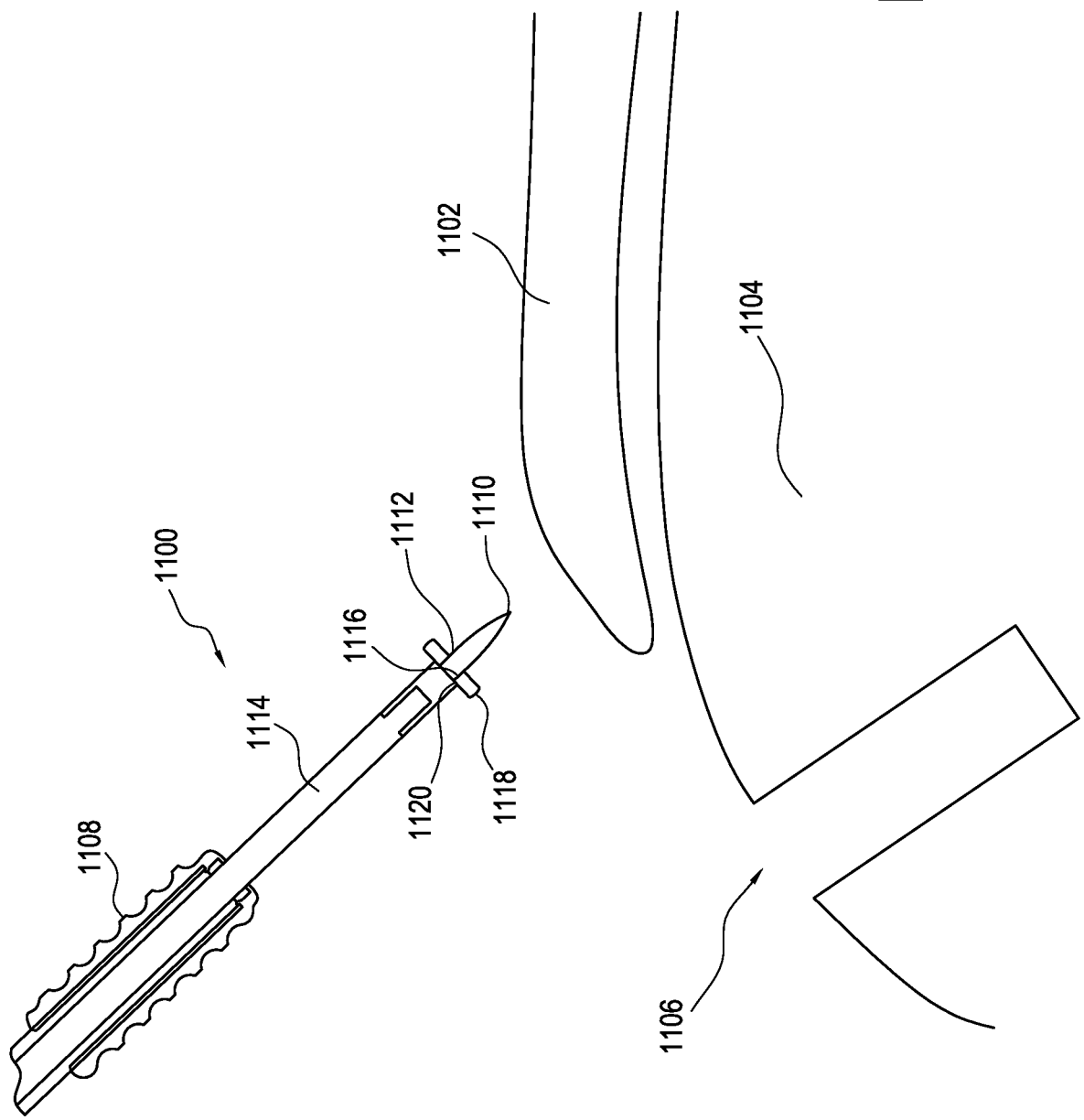

FIGS. 11A-11H show, in schematic cross-sectional view, various states in an exemplary method of using a surgical tool 1100 similar to tool 1000 of FIGS. 10A and 10B. FIG. 11A shows surgical tool 1100, a portion of a detached tendon 1102 and a portion of a bony substrate 1104 where the tendon is to be reattached. As illustrated, a bore 1106 has been prepared in the bony substrate to receive a portion of the tendon and a bone anchor 1108.

It will be noted that a distal end 1110 of the surgical tool is pointed for piercing, and that a circumferential external surface 1112 of a shaft 1114 of the surgical tool 1100 (or of a separate tip on the shaft 1114) supports a corresponding internal surface 1116 of a bearing washer 1118. It will also be noted that the bearing washer 1118 is prevented from moving proximally along shaft 1114 by a shoulder feature 1120, and that the surgical tool 1100 is disposed in an extended configuration (as discussed in relation to FIGS. 10A-10B).

Figure 11B:
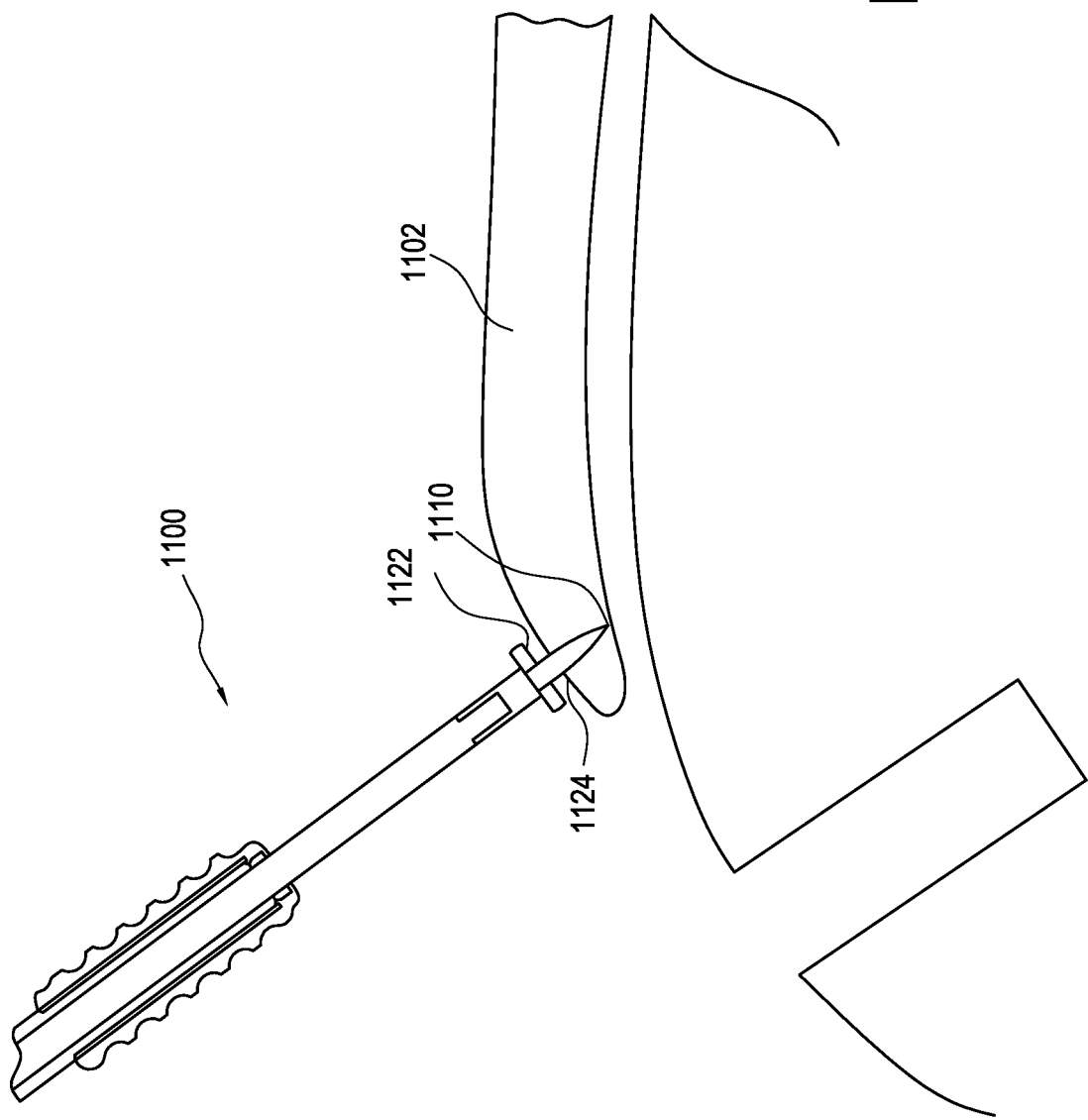

FIG. 11B shows that the surgical tool 1100 has been advanced so that distal end 1110 has pierced the tendon 1102. According to an exemplary method, tool 1100 is urged forward longitudinally until a distal surface region 1122 of bearing washer 1118 contacts a corresponding surface region 1124 of tendon 1102.

FIG. 11C shows that surgical tool 1100 has been rotated 1126 about an axis transverse to longitudinal axis 1128 of shaft 1114, and advanced 1130 towards the prepared bore 1106. Tendon 1102 is consequently moved with respect to bony substrate 1104 and stretched towards a desired attachment location.

Figure 11D:
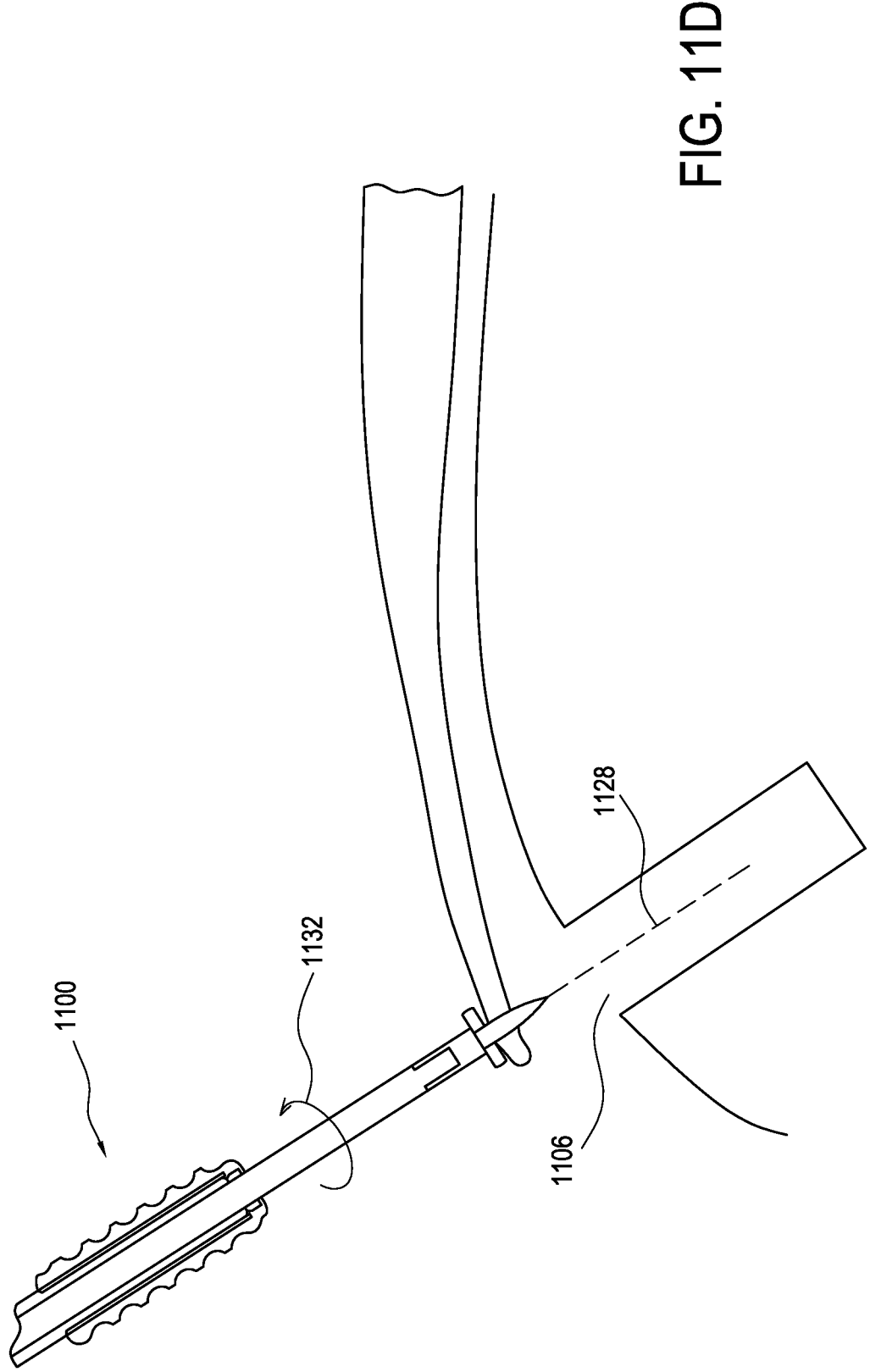

Thereafter, as shown in FIG. 11D surgical tool 1100 is counter-rotated 1132 to bring longitudinal axis 1128 generally into alignment with a longitudinal axis of bore 1106.

Figure 11E:
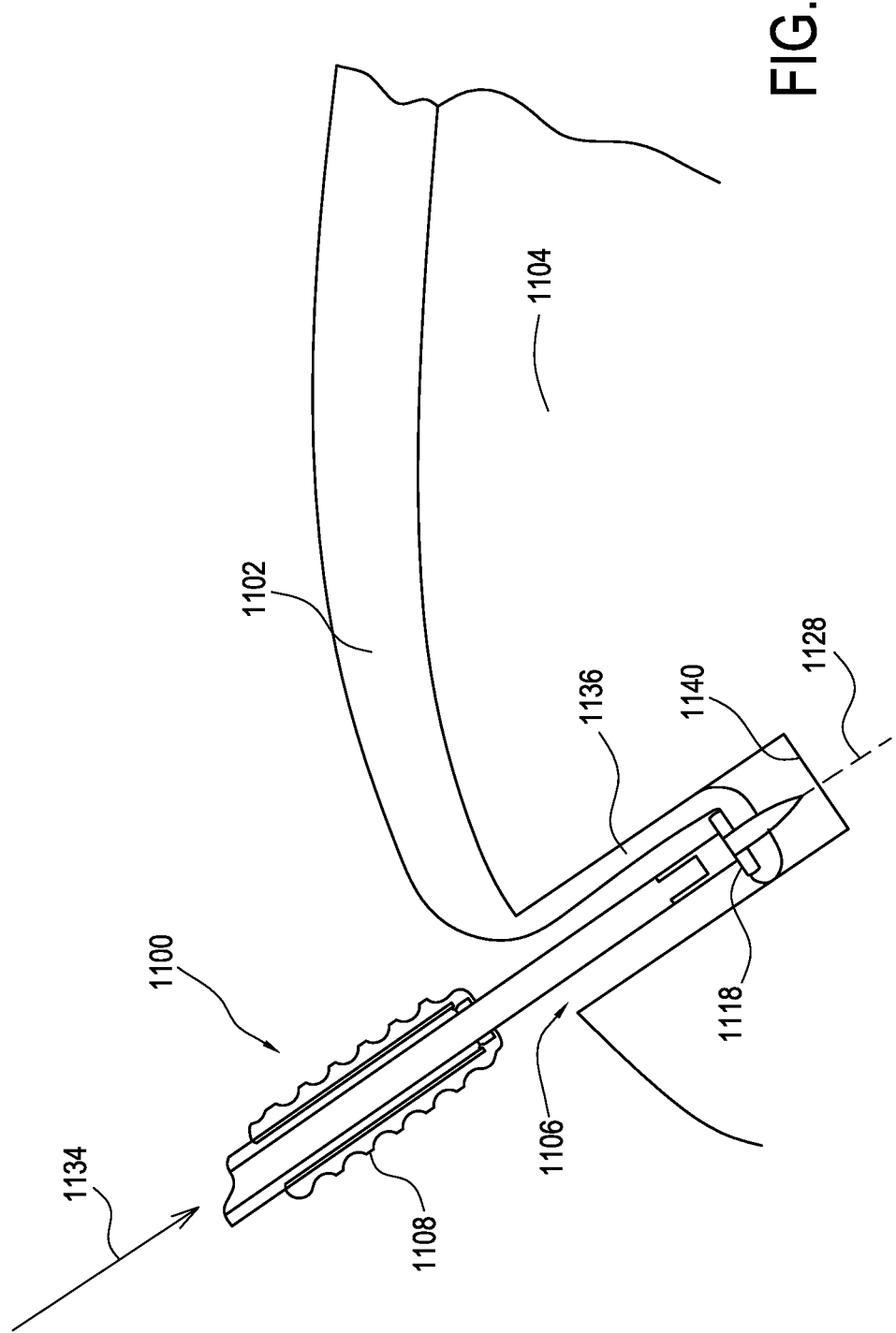

Thereafter, surgical tool 1100 is advanced with a generally linear motion in direction 1134 along longitudinal axis 1128 to draw a portion 1136 of tendon 1102 into and towards the bottom surface 1140 of bore 1106, as shown in FIG. 11E. Once the tendon portion 1136 has been advanced to a desired location within bore 1106, a detent of the surgical tool is released. This allows relative longitudinal displacement of the bone anchor 1108 in direction 1134 with respect to the substrate bone 1104 and the washer 1118.

Figure 11F:
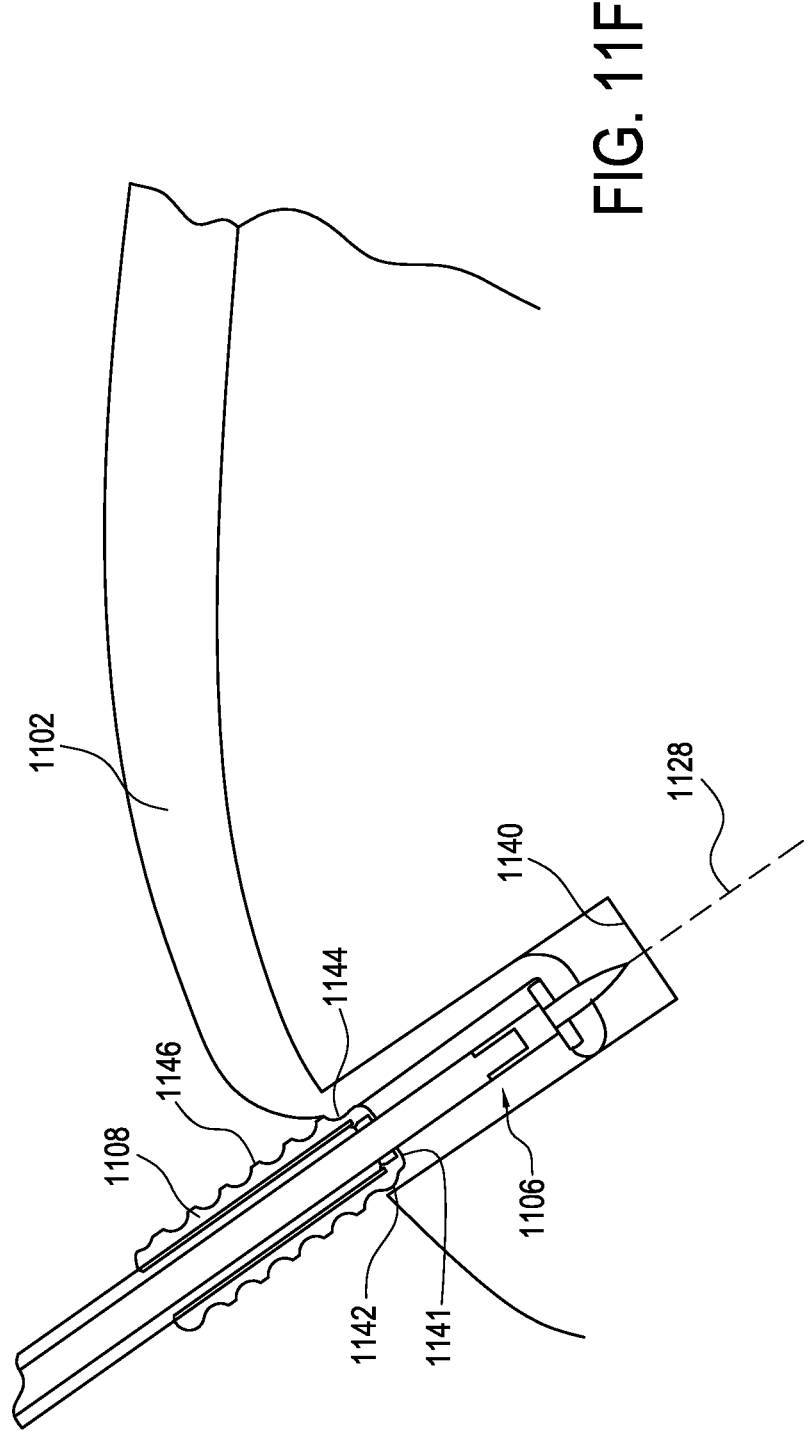

FIG. 11F shows a state of the surgical tool, in which a distal end 1141 of the bone anchor 1108 has been advanced into contact with a proximal edge 1142 of bore 1106 (i.e., the mouth of the bore), and into contact with a surface region 1144 the tendon 1102. This brings helical threads e.g., 1146, of the bone anchor 1108 into an arrangement where rotation of the bone anchor 1108 about longitudinal axis 1128 causes the threads of the bone anchor to further engage with the surrounding bone and soft tissue so as to advance the bone anchor towards the bottom 1140 of the bore 1106.

Figure 11G:
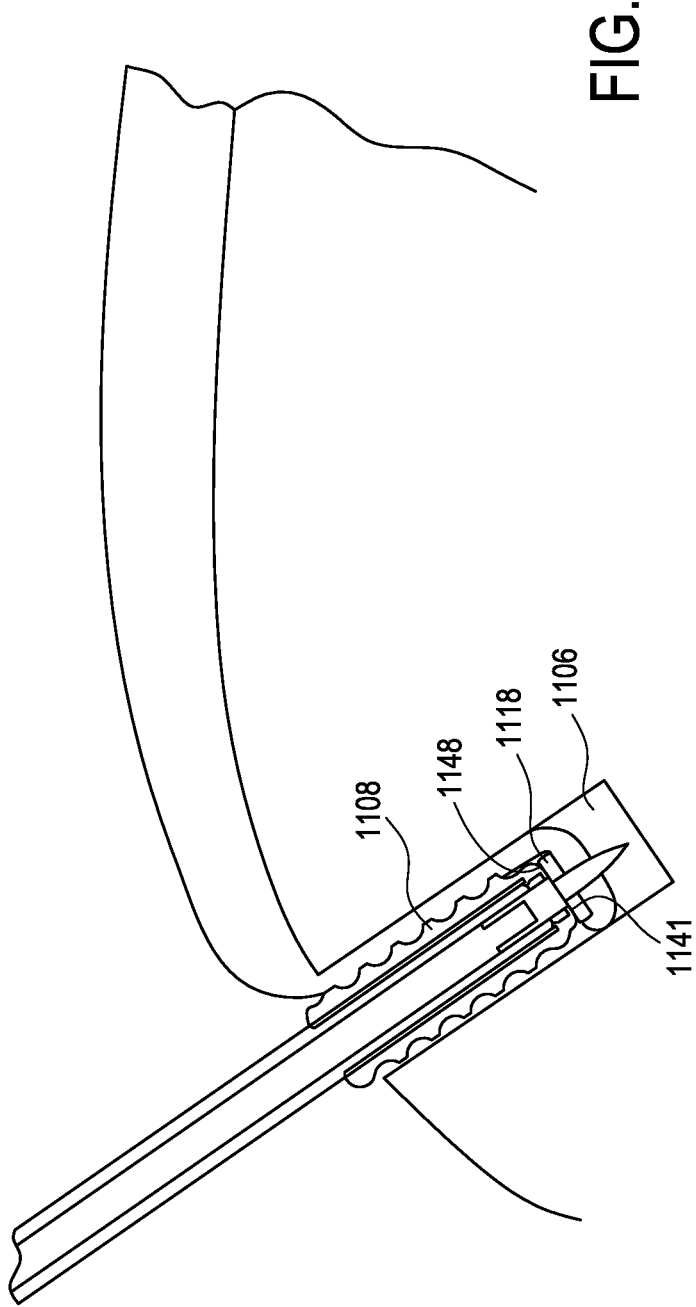
Figure 11H:
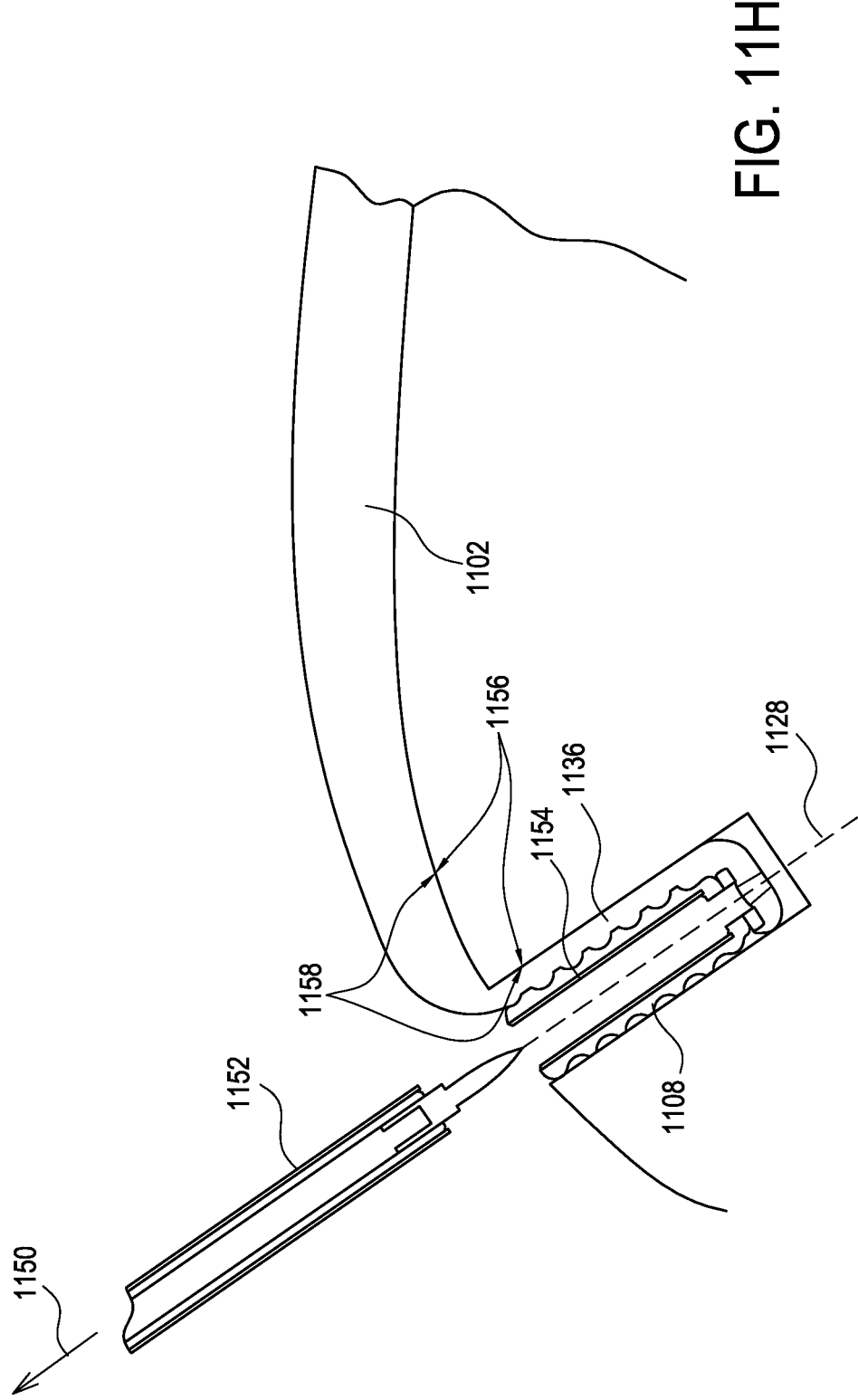

FIG. 11G shows a condition of the assembly once the bone anchor 1108 has been rotated until fully driven into the bore 1106, such that the distal end 1141 of the bone anchor 1108 is disposed in contact with a proximal surface region 1148 of bearing washer 1118. Thereafter, as shown in FIG. 11H, the surgical tool may be withdrawn in direction 1150 along longitudinal axis 1128.

This causes the respective spline features 1152, 1154 of the surgical tool 1100 to disengage. The surgical tool is removed and the bone anchor 1108 and tendon 1102, 1136 are fixed in place. One of skill in the art will appreciate that this arrangement will hold a surface region 1156 of the tendon in direct contact with a corresponding surface region 1158 of the substrate bone, allowing regrowth and reattachment of the soft tissue and bone.

While ligament and bone have been identified in the foregoing discussion for illustrative purposes, one of skill in the art will appreciate that any variety of soft tissues and hard tissues will be joined according to the identified methods and using the identified apparatus in various combinations.

In an alternative arrangement, a surgical tool such as surgical tool 1100 (FIG. 11) is configured to be employed by passing a suture through soft tissue 1102, and wrapping the suture around a circumferential external surface 1112 of shaft 1114. The suture is then urged into bore 1106 and fixed in place by the application of the anchor 1108.

Figure 12:
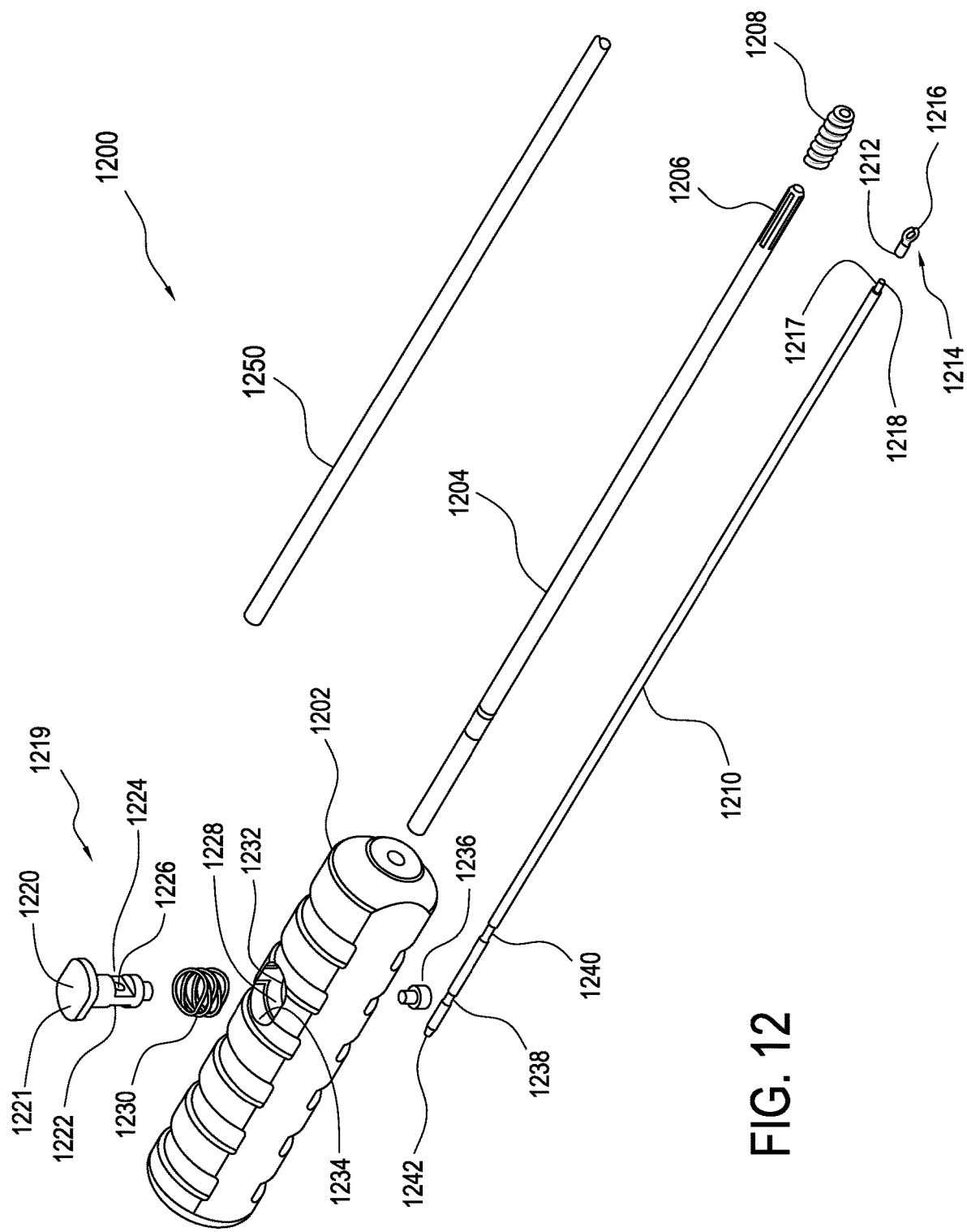
FIG. 12 shows, in exploded view, an exemplary surgical tool according to principles of the invention.

FIG. 12 shows, in exploded perspective view, an exemplary surgical tool 1200 prepared according to principles of the invention. The surgical tool 1200 includes a handle member 1202. The handle member 1202 is substantially fixedly coupled to a cannulated anchor driver 1204 such that a longitudinal axis of the handle member and a longitudinal axis of the cannulated anchor driver are substantially coincident.

The cannulated anchor driver 1204 includes, on an external circumferential surface of its distal end, a spline feature 1206. The spline feature 1206 is sized and arrange to couple with, and be complementary to, an internal spline feature of a bone anchor 1208. The bone anchor 1208 is shown as having an external helical thread for engaging with an internal circumferential surface of a bore in a substrate. One of skill in the art will appreciate that any of the bone anchors presented in this application need not be helically threaded, but may include any of a wide variety of bone anchors including, for example and without limitation, a barbed bone anchor, an adhesively mounted bone anchor, and any combination thereof.

Disposed within a longitudinal cannula (or bore) of the cannulated anchored driver 1204 is a suture guide shaft 1210. The suture guide shaft is substantially fixedly coupled, at a distal end thereof, to a suture guide 1212. The suture guide includes, at its distal end, a generally toroidal feature 1214 such as, for example, an eyelet. The toroidal feature defines an aperture 1216 with an internal bearing surface region for encircling and controlling a portion of a suture or other material. The longitudinal axis of the suture guide shaft 1210 lies generally within a plane of the aperture 1216. A longitudinal axis of the aperture through the plane of the aperture is disposed generally transverse to the longitudinal axis of the suture guide shaft 1210. When the suture guide shaft 1210 is in use, it is disposed within the cannula of the cannulated anchor driver 1204, such that the cannulated anchor driver at the suture guide shaft are arranged generally coaxial to one another.

In the illustrated embodiment, the suture guide shaft 1210 includes, near its distal end, an externally threaded coupling feature 1218 and suture guide support shoulder 1217. These serve to substantially fixedly couple the suture guide shaft 1210 to the suture guide 1212. One of skill in the art will understand that, in various embodiments, the suture guide shaft 1210 and suture guide 1212 will be coupled in any effective way known, or that becomes known, in the art. Moreover, in certain embodiments, the suture guide shaft 1210 and suture guide 1212 will be integrally formed as a single component.

Also illustrated are components of a detent mechanism 1219 of the surgical tool 1200. These include a release button member 1220, having a generally planar upper surface region 1221 and a detent shaft 1222 with a generally cylindrical external surface region. A detent shaft relief feature 1224 describes a recess formed in the detent shaft 1222. The release button member 1220 also includes a suture guide shaft aperture 1226 disposed through the detent shaft 1222 within the detent shaft relief feature 1224 and generally transverse to a longitudinal axis of the release button member 1220.

The handle member 1202 includes a detent shaft aperture 1228 with the longitudinal axis generally transverse to the longitudinal axis of the surgical tool handle member 1202. The detent shaft aperture 1228 is configured to receive the detent shaft 1222 slidingly therewithin. A detent spring 1230 is sized and configured to be disposed within a recess 1232 arranged within the handle member 1202 coaxially around detent shaft aperture 1228. As will be evident to the reader, the detent shaft 1222 is sized and configured to be disposed within an internal region defined by the detent spring 1230.

The illustrated detent spring 1230 is shown as a plurality of Belleville washers. One of skill in the art will appreciate, that other configurations, including any spiral spring, elastomeric tube, or other elastic member will be used in corresponding embodiments of the invention according to the requirements of a particular application.

The recess 1232 is defined by an internal surface region of a suture guide release button relief 1234, such that the release button member 1220 can move radially into the handle by compression of spring 1230 when an inward radial force is applied to upper surface region 1221.

A detent shaft retainer fastener 1236 is configured to be coupled to a lower end of the release button member 1220 (e.g., by a threaded coupling, a weldment, a chemical adhesive, etc.) so as to retain the release button member 1220 and detent spring 1230 in place.

As illustrated, the suture guide shaft 1210 includes first 1238 and second 1240 capture relief features near a proximal end of the suture guide shaft. The suture guide shaft 1210 also includes a tapered feature 1242 immediately adjacent its proximal end. As will be further discussed and illustrated below, first 1238 and second 1240 capture relief features are arranged and configured to be releasably captured at the detent shaft relief feature 1224 when the suture guide shaft 1210 is disposed within the suture guide shaft aperture 1226 of the detent shaft 1222.

As illustrated, in certain embodiments a further sheath 1250 is disposed coaxially around the outside of cannulated anchor driver 1204.

Figure 13:
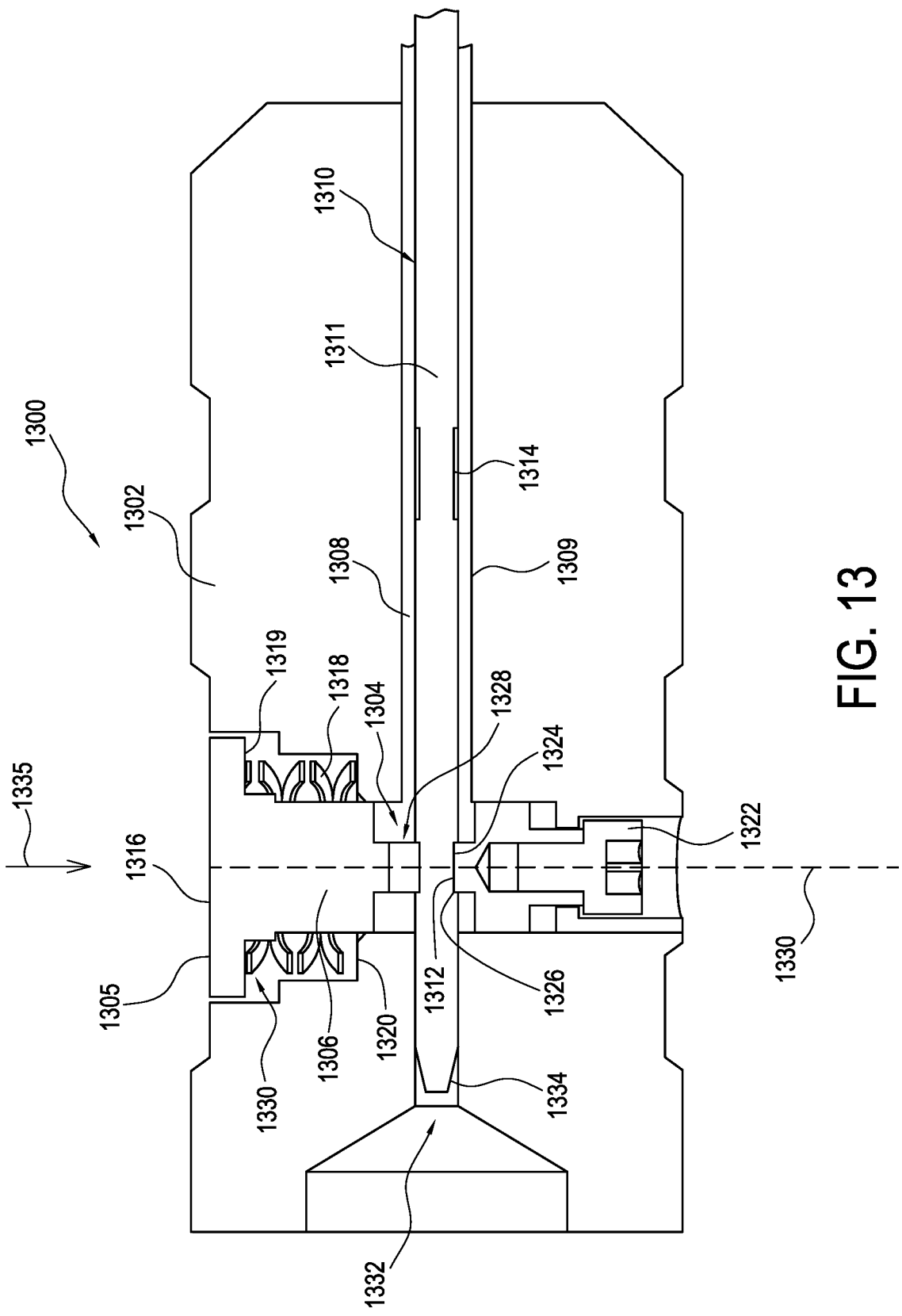
FIG. 13 shows, in schematic cross-section, a handle portion of a surgical tool prepared according to principles of the invention.

FIG. 13 shows, in cross-section, a portion of an exemplary surgical tool 1300 prepared according to principles of the invention. Surgical tool 1300 includes a handle member 1302 with a detent shaft aperture 1304. A detent member 1305 including a detent shaft 1306 is disposed coaxially within the detent shaft aperture 1304. Transverse to the detent shaft aperture 1304, a cannulated anchor driver 1308 is substantially fixedly disposed coaxially within a further bore 1309 of the handle member 1302.

Slidingly disposed within a cannula 1310 of the cannulated anchor driver 1308 is a suture guide shaft 1311. The guide shaft is relieved at two locations along its length; an extended guide shaft relief 1312, and a retracted guide shaft relief 1314. One of skill in the art will readily understand that the guide shaft is adapted to be arrested in its longitudinal motion by a detent mechanism of the handle at either of the extended guide shaft relief 1312 and the retracted guide shaft relief 1314.

The suture guide shaft 1311, is rotatable within the cannula 1310 when captured by the detent mechanism at both of the extended configuration and the retracted configuration. That is, the handle member 1302 can be co-rotated with the cannulated anchor driver 1308 about a longitudinal axis common to the handle, the cannulated anchor driver 1308 and the suture guide shaft 1311 while the suture guide shaft 1311 remains static and does not rotate. In order to allow this relative rotation of the handle member 1302 and cannulated anchor driver 1308 with respect to the suture guide shaft 1311, the cross-sections of the suture guide shaft 1311 and both the extended 1312 and retracted 1314 reliefs of the suture guide shaft are substantially circular.

In other embodiments, the detent mechanism is arranged to prevent rotation of the suture guide with respect to the cannulated anchor driver until the detent mechanism is released.

The detent member 1305 includes a suture guide release button 1316. One end of a detent spring 1318 is located proximal to a lower surface 1319 of the suture guide release button 1316. An opposite end of the detent spring 1318 is supported by a detent spring shoulder 1320. The detent spring 1318 is arranged to urge the lower surface 1319 of the suture guide release button 1316 away from the detent spring shoulder 1320. This motion is limited by a detent shaft retainer fastener 1322 in a manner that will be evident to one of skill in the art.

Detent shaft 1306 includes a detent shaft aperture 1328 which is located substantially perpendicular to a longitudinal axis 1330 of the detent shaft 1306. By urging the lower surface 1319 of the suture guide release button 1316 away from the detent spring shoulder 1320, the detent spring 1318 tends to maintain circumferential edges 1324, 1326 of the detent shaft aperture 1328 in contact with corresponding edge regions of the guide shaft reliefs 1312, 1314 so as to temporarily substantially fix the longitudinal position of the suture guide shaft 1311 with respect to the handle 1302 and cannulated anchor driver 1308.

It will be noted that a proximal end 1332 of the suture guide shaft 1311 includes a generally conically tapered region 1334. This conically tapered region 1334 facilitates initial insertion of the suture guide shaft 1311 into the apparatus and past edge 1324 of the detent shaft aperture 1328.

Upon inspection, it will be clear to one of skill in the art that, when the surgical tool 1300 is in use, urging the suture guide release button 1316 inwardly 1335 will tend to release the engagement of circumferential edges 1324 and 1326 from the extended guide shaft relief 1312 so that the suture guide shaft 1311 can slide longitudinally and distally within cannula 1310. If the suture guide release button 1316 is thereafter released, when suture guide release 1314 arrives at the detent shaft aperture 1328, the action of detent spring 1318 will urge the detent shaft into engagement with retracted relief 1314. This corresponds to the action of the surgical tool, as described above.

Figure 14:
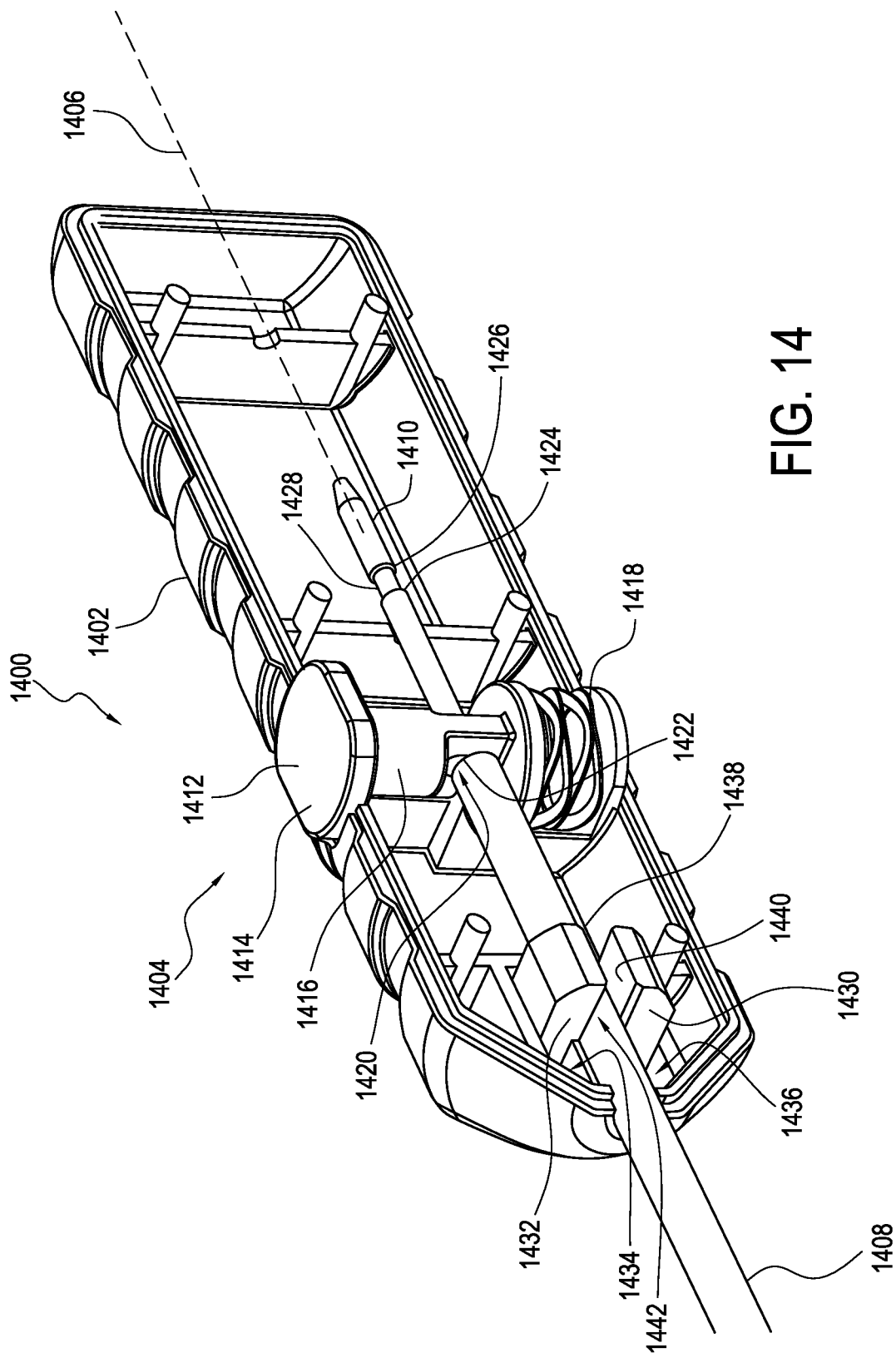
FIG. 14 shows, in schematic cross-section, a surgical tool prepared according to principles of the invention.

FIG. 14 shows, in schematic perspective view, another aspect of a surgical tool 1400 prepared according to principles of the invention. The surgical tool 1400 includes a handle member 1402. Disposed within the handle member 1402 is a detent mechanism 1404. A longitudinal axis 1406 is common to the handle member 1402, a cannulated anchor driver 1408 and a suture guide shaft 1410 disposed within a cannula of the cannulated anchor driver 1408.

The detent mechanism 1404 includes a detent member 1412 with a suture guide release button 1414 a detent shaft 1416 detent spring 1418 and a suture guide aperture 1420. In the manner discussed above, the suture guide aperture 1420 embodies edges 1422 that interfere with and temporarily capture corresponding edges e.g., 1424, 1426 of an extended suture guide relief 1428, and a retracted suture guide relief (not visible).

It will be noted that, in contrast to surgical tool 1300 of FIG. 13, detent spring 1418 of surgical tool 1400 is disposed relatively distal to release button 1414 of detent member 1412, as compared to detent spring 1318 and release button 1316.

Handle member 1402 also includes first 1430 and second 1432 distal jaw members. Distal jaw members 1430 and 1432 are disposed within respective recesses 1434, 1436 of handle member 1402. The jaw members 1430 and 1432 have respective contact surface regions 1438, 1440. In the illustrated embodiment, cannulated anchor driver 1408 includes jaw apertures, e.g. 1442.

In certain embodiments of the invention, distal jaw members 1430 and 1432 tend to impinge within the jaw apertures, e.g. 1442, to retain cannulated anchor driver 1408 longitudinally and rotationally in place within the handle member 1402. In such embodiments, cannulated anchor driver 1408 may be removably installed within handle member 1402 and securely retained therein during operation of the surgical tool 1400.

In certain embodiments, the contact surface regions 1438 and 1440 are arranged to impinge on an external circumferential surface region of suture guide shaft 1410, thereby providing a desirable resistance to rotation of the suture guide shaft 1410 with respect to handle member 1402 while still allowing the suture guide shaft to rotate.

In various embodiments of the invention, the distal jaw members 1430 and 1432 include one or more of an elastomeric polymer material, a thermoplastic polymer material, a thermoset polymer material, and a metallic material. In other embodiments, other materials will be employed to achieve desirable characteristics to achieve the functions described above.

A method according to principles of the invention includes:
1. Place sutures through the targeted tissue as required.
2. Create a hole to accommodate the selected diameter anchor to the proper depth using a purpose designed drill bit and guide. The guide may or may not be required.
3. Aseptically open the driver and anchor and place the anchor onto the driver.
4. Thread previously placed sutures placed through the Suture Guide located on the distal end of the driver.
5. Insert the Suture Guide with handle into the hole created in step 2.
6. Remove any slack in the suture and create the desired amount of tension by pulling on the suture tails.
7. Push the handle with the anchor firmly into the hole, until the anchor contacts the suture. This action will maintain the desired tension on the suture.
8. Depress the button on the handle and begin to insert the anchor into the hole by turning the handle in a clockwise direction.

9. Continue insertion until an audible "click" is heard. This will signal the proper depth of the implant, which should be slightly below the surface of the surrounding bone.
10. Remove the handle from the implant by pulling it along the axis of insertion.
11. Trim the access suture tails as desired.

While the invention has been described in detail in connection with the presently preferred embodiments, it should be readily understood that the invention is not limited to such disclosed embodiments. Rather, the invention can be modified to incorporate any number of variations, alterations, substitutions, or equivalent arrangements not heretofore described, but which are commensurate with the spirit and scope of the invention. Accordingly, the invention is not to be seen as limited by the foregoing description, but is only limited by the scope of the appended claims.

The invention claimed is:

1. A surgical tool comprising:
   a cannulated anchor driver;
   a suture guide shaft, a portion of said suture guide shaft being disposed coaxially within a cannula of said cannulated anchor driver, said suture guide shaft having a suture guide disposed at a distal end thereof, said suture guide having an internal circumferential surface region and an external circumferential surface region, said internal circumferential surface region defining an aperture through said suture guide, said internal circumferential surface region being initially contiguous, said suture guide having a frangible portion disposed between said external circumferential surface region and said internal circumferential surface region;
   an anchor, said anchor being temporarily coupled to said cannulated anchor driver, said anchor having a distal end, said distal end being adapted to interfere with a portion of said external circumferential surface region as said suture guide is moved towards said cannula of said cannulated anchor driver, thereby distorting said aperture and causing said frangible portion to fracture.

2. The surgical tool as defined in claim 1 wherein said suture guide includes a generally toroidal portion.

3. The surgical tool as defined in claim 1 wherein said internal circumferential surface region comprises a bearing surface.

4. The surgical tool as defined in claim 1 wherein said anchor includes spline features and wherein said anchor is slidingly coupled to said cannulated anchor driver.

5. The surgical tool as defined in claim 1 wherein said anchor is adapted to capture a portion of a suture, and wherein said portion of said suture is adapted to be released from said suture guide by said fracture of said frangible portion.

6. The surgical tool as defined in claim 1 wherein said suture guide is coupled to said suture guide shaft.

7. The surgical tool as defined in claim 1 wherein said suture guide is relieved in a vicinity of said frangible portion.

8. The surgical tool as defined in claim 1 further comprising:
   a handle, said handle including a detent mechanism, said handle being substantially fixedly coupled to said cannulated anchor driver, said detent mechanism being releasably coupled to said suture guide shaft such that said suture guide is retracted towards said cannula of said cannulated anchor driver responsive to operation of said detent mechanism.

9. The surgical tool as defined in claim 1 wherein said external surface region comprises a polygonal section.

10. The surgical tool as defined in claim 1 further comprising:
    a portion of a suture disposed within said aperture.

* * * * *